(12) United States Patent
Benarous et al.

(10) Patent No.: US 6,730,486 B1
(45) Date of Patent: May 4, 2004

(54) HUMAN βTRCP PROTEIN

(75) Inventors: Richard Benarous, Paris (FR); Florence Margottin, Paris (FR); Hervé Durand, Bouray/Juine (FR); Fernando Arenzana Seisdedos, Meudon (FR); Mathias Kroll, Paris (FR); Jean-Paul Concordet, Vincennes (FR)

(73) Assignees: Institut National de la Sante et de la Recherche Medicale, Paris Cedex (FR); Institut Pasteur, Paris (FR)

( * ) Notice: Subject to any disclaimer, the term of this patent is extended or adjusted under 35 U.S.C. 154(b) by 0 days.

(21) Appl. No.: 09/601,168
(22) PCT Filed: Jan. 29, 1999
(86) PCT No.: PCT/FR99/00196
§ 371 (c)(1),
(2), (4) Date: Jul. 28, 2000
(87) PCT Pub. No.: WO99/38969
PCT Pub. Date: Aug. 5, 1999

(30) Foreign Application Priority Data

Jan. 30, 1998 (FR) .............................. 98 01100
Dec. 9, 1998 (FR) .............................. 98 15545

(51) Int. Cl.$^7$ ........................ C07K 14/00; C07H 21/02; C07H 21/04; C12Q 1/00; C12N 15/09
(52) U.S. Cl. ........................ 435/7.1; 435/4; 435/252.3; 435/320.1; 514/2; 530/350; 536/23.1; 930/10
(58) Field of Search ........................ 530/350; 536/23.1; 514/2; 435/4, 7.1, 252.3, 320.1; 930/10

(56) References Cited

PUBLICATIONS

Spevak et al. *Saccharomyces cerevisiae* cdc 15 Mutants Arrested at a Late Stage in Anaphase are Rescued by Xenopus cDNAs Encoding N–ras or a Protein with Beta–Transducin Repeats. Mol. Cell Biol. 13(8): 4953–4966 (Aug. 1993).*
Bowie et al. Deciphering the message in protein sequences: tolerance to amino acid substitutions. 1990, Science, vol. 247, No. 4948, pp. 1306–1310.*
Ngo et al. "Computational Complexity, Protein Structure Prediction, and the Levinthal Paradox " in The Protein Folding Problem and Tertiary Structure, 1994, Merz et al. ed. Birkhauser, Boston., pp. 491–495.*
Wells et al. Additivity of Mutational Effects in Proteins, 1990, Biochemistry, vol. 29, pp. 8509–8517.*
Inoue et al. Direct Association of pp40/lkappaBbeta iwth rel/NF–kappaB transcription factors: Role of ankyrin repeats in the inhibition of DNA binding activity, 1992, Proc. Natl. Acad. Sci. vol. 89, pp. 4333–4337.*
Rubinfeld et al. The APC Protein and E–cadherin Form Similar but Independent Complexes with alpha–Catenin, beta–Catenin, and Plakoglobin. 1995, J. Biol. Chem. vol. 270, No. 10, pp. 5549–5555.*
Skowyra et al. F–Box Proteins are Receptors that Recruit Phosphorylated Substrates to the SCF Ubiquitin–Ligase Complex, 1997, Cell, vol. 91, pp. 209–219.*
Bour et al. The Human Immunodeficiency Virus Type 1 Vpu Protein Specifically Binds to the Cytoplasmic Domain of CD4; Implications for the Mechanism of Degradation, 1995, J. Virol. vol. 69, No. 3, pp. 1510–1520.*

* cited by examiner

*Primary Examiner*—Christopher S. F. Low
*Assistant Examiner*—Holly Schnizer
(74) *Attorney, Agent, or Firm*—Antonelli, Terry, Stout & Kraus, LLP

(57) ABSTRACT

The present invention relates to the human βTrCP protein for the targeting of proteins towards proteasome degradation pathways, which is capable of interacting with the Vpu protein of HIV-1 virus, with the cell proteins IκB and β-catenin and with the cell protein Skp1p, to its peptide fragments and to the nucleic acid sequences coding for said protein and its fragments.

It further relates to the use of the human β-TrCP protein or its peptide fragments for the screening of anti-HIV-1 antiviral agents, antitumoral agents and anti-inflammatory agents, to the antiviral agents, antitumoral agents and anti-inflammatory agents, and to the antibodies directed against said protein and its peptide fragments.

7 Claims, 13 Drawing Sheets

```
                                                                          *
                        *  ******
                        MDPAEAVLQEKALKFMN------------------------------SSEREDCNNGEPPRKI    33
                        MEGFSCSLQPPT----------------------------------ASEREDCNRDEPPRKI    28
                        MRRERQRMMSFEDKDKDDLDNSNSNNSSEMTDTAMPPLKRLLITGSSDDLAQGSSGKKK    60
                        MSSVLMSKTVTPFLREHIPSIYAPIGKPGNQETARAENPN-----------------    40
                            *  ****      *****                                                *
                        IPEKNSLRQTYNSCARLCLNQETVCLASTAMKTENCVAKTKLANGTSSMIVPKR------    88
                        ITE------------------------------KNTLRQTKLANGTSSMIVPKR------    53
                        LTMATRSPSSSPDLATNDSGTRVQPLPEYNFTKFCYRHNPDIQFSPTHTACYKDLKRTQ   120
                        ---------------------------------SKYCYRHPD------SKCRRAADKAKMV    63
                                *
                        ------------KLSTSYEREKELCVKYFEQWSESDQVEEVERDISQMCH----------   126
                        ------------KLSNYEKEKELCVKYFEQWSECDQVEEVERDISRMCH----------    91
                        EINANIAKLPLQEQSDIHHIISKYSNSNDKIRKLILDGILSTSCFPQLSYISSLVTHM---   178
                        MIQSELDKLTSADQQAVTHWSLFSAAPARHRDMLQGILSQLCFPQLSEVSREVNEA---   121
                                                           F-BOX                   *
                        YQHGHINSYLKPMIQRDFITAEPARGLDHIAENIISYLDAKSLGAELVGKEMYRVTSDG   186
                        YQHGHINTYLKPMIQRDFITAEPARGLDHIAENIISYLDAKSLGSAELVGKEMYRVTSDG  151
                        ------------IKIDFISIMQE-----LSLKIKSYLDCQSLGMATRVQRKWQKLADDD   221
                        ------------LKIDELSANVE-----LAQKVLCVLDTVSLTKQAQMSQRMRTLADSD   164
                                                                             **
                        MLWKKLIERMVRTDSLWRGLAERRC GQYIFKNKPPDGNAPPNSFYRALYPKIIQDIET-   245
                        MLWKKLIERMVRTDSLWRGLAERRMGQYLFKNKPPDGKTPPNSFYRALYPKIIQDIET-   210
                        RVWYRMCEQHI------DRKCPNCGWGLPLLHMK--RARIQQNSTGSSNADIQTQT---   270
                        AVWVRMCEQHU------NRKCTKCGWGLPLLERKKLRNYTRQRQLAKGGPQGRVTELLADS   218
                        ----------------------------------------------------IES      248
                        ----------------------------------------------------IES      213
                        ----------------------------------------------TRPWKVIYRERFKVES   286
                        HDSQDRSVNQHGKRPAAEAEEEDPIKKRQCMAAAEASKAVTQPKTRSWKAVYRDRWQVSY  278
```

| | LexA-hybrid | Gal4AD-hybrid | +His | -His | β-gal | β-Gal units |
|---|---|---|---|---|---|---|
| 1 | Skp1p | + h-βTrCP | | | | 18 |
| 2 | Skp1p | + h-βTrCP-Δ7W | | | | 124 |
| 3 | Skp1p | + VBP1 | | | | 2 |
| 4 | Skp1p | + CD4c | | | | 2 |

FIG. 4

| LexA BD | Gal4 AD | +His | -His | β-Gal |
|---|---|---|---|---|
| βTrCP | IκBα | | | |
| βTrCP | IκBα S32-36A | | | |
| βTrCP | Raf | | | |
| Ras | IκBα | | | |
| βTrCP | Vpu$_c$ | | | |
| Ras | Raf | | | |

FIG. 6

SEQUENCE LISTING

```
<160> NUMBER OF SEQ ID NOS: 9

<210> SEQ ID NO 1
<211> LENGTH: 2151
<212> TYPE: DNA
<213> ORGANISM: Artificial sequence
<220> FEATURE:
<221> NAME/KEY: CDS
<222> LOCATION: (70)..(1776)
<220> FEATURE:
<223> OTHER INFORMATION: Description of the artificial sequence : cDNA
      coding for human beta-TrCP protein

<400> SEQUENCE: 1
tgcgttggct gcggcctggc accaaagggg cggccccggc ggagagcgga cccagtggcc      60 tcggcgatt atg gac ccg gcc gag gcg gtg ctg caa gag aag gca ctc aag     111
            Met Asp Pro Ala Glu Ala Val Leu Gln Glu Lys Ala Leu Lys
            1               5                   10 ttt atg aat tcc tca gag aga gaa gac tgt aat aat ggc gaa ccc cct       159
Phe Met Asn Ser Ser Glu Arg Glu Asp Cys Asn Asn Gly Glu Pro Pro
 15                  20                  25                  30 agg aag ata ata cca gag aag aat tca ctt aga cag aca tac aac agc       207
Arg Lys Ile Ile Pro Glu Lys Asn Ser Leu Arg Gln Thr Tyr Asn Ser
```

-continued

|  |  |  | 35 |  |  |  | 40 |  |  |  | 45 |  |  |  |  |
|---|---|---|---|---|---|---|---|---|---|---|---|---|---|---|---|

```
tgt gcc aga ctc tgc tta aac caa gaa aca gta tgt tta gca agc act       255
Cys Ala Arg Leu Cys Leu Asn Gln Glu Thr Val Cys Leu Ala Ser Thr
             50                  55                  60 gct atg aag act gag aat tgt gtg gcc aaa aca aaa ctt gcc aat ggc       303
Ala Met Lys Thr Glu Asn Cys Val Ala Lys Thr Lys Leu Ala Asn Gly
         65                  70                  75 act tcc agt atg att gtg ccc aag caa cgg aaa ctc tca gca agc tat       351
Thr Ser Ser Met Ile Val Pro Lys Gln Arg Lys Leu Ser Ala Ser Tyr
     80                  85                  90 gaa aag gaa aag gaa ctg tgt gtc aaa tac ttt gag cag tgg tca gag       399
Glu Lys Glu Lys Glu Leu Cys Val Lys Tyr Phe Glu Gln Trp Ser Glu
 95                 100                 105                 110 tca gat caa gtg gaa ttt gtg gaa cat ctt ata tcc caa atg tgt cat       447
Ser Asp Gln Val Glu Phe Val Glu His Leu Ile Ser Gln Met Cys His
                115                 120                 125 tac caa cat ggg cac ata aac tcg tat ctt aaa cct atg ttg cag aga       495
Tyr Gln His Gly His Ile Asn Ser Tyr Leu Lys Pro Met Leu Gln Arg
            130                 135                 140 gat ttc ata act gct ctg cca gct cgg gga ttg gat cat atc gct gag       543
Asp Phe Ile Thr Ala Leu Pro Ala Arg Gly Leu Asp His Ile Ala Glu
        145                 150                 155 aac att ctg tca tac ctg gat gcc aaa tca cta tgt gct gct gaa ctt       591
Asn Ile Leu Ser Tyr Leu Asp Ala Lys Ser Leu Cys Ala Ala Glu Leu
    160                 165                 170 gtg tgc aag gaa tgg tac cga gtg acc tct gat ggc atg ctg tgg aag       639
Val Cys Lys Glu Trp Tyr Arg Val Thr Ser Asp Gly Met Leu Trp Lys
175                 180                 185                 190 aag ctt atc gag aga atg gtc agg aca gat tct ctg tgg aga ggc ctg       687
Lys Leu Ile Glu Arg Met Val Arg Thr Asp Ser Leu Trp Arg Gly Leu
                195                 200                 205 gca gaa cga aga gga tgg gga cag tat tta ttc aaa aac aaa cct cct       735
Ala Glu Arg Arg Gly Trp Gly Gln Tyr Leu Phe Lys Asn Lys Pro Pro
            210                 215                 220 gac ggg aat gct cct ccc aac tct ttt tat aga gca ctt tat cct aaa       783
Asp Gly Asn Ala Pro Pro Asn Ser Phe Tyr Arg Ala Leu Tyr Pro Lys
        225                 230                 235 att ata caa gac att gag aca ata gaa tct aat tgg aga tgt gga aga       831
Ile Ile Gln Asp Ile Glu Thr Ile Glu Ser Asn Trp Arg Cys Gly Arg
    240                 245                 250 cat agt tta cag aga att cac tgc cga agt gaa aca agc aaa gga gtt       879
His Ser Leu Gln Arg Ile His Cys Arg Ser Glu Thr Ser Lys Gly Val
255                 260                 265                 270 tac tgt tta cag tat gat gat cag aaa ata gta agc ggc ctt cga gac       927
Tyr Cys Leu Gln Tyr Asp Asp Gln Lys Ile Val Ser Gly Leu Arg Asp
                275                 280                 285 aac aca atc aag atc tgg gat aaa aac aca ttg gaa tgc aag cga att       975
Asn Thr Ile Lys Ile Trp Asp Lys Asn Thr Leu Glu Cys Lys Arg Ile
            290                 295                 300 ctc aca ggc cat aca ggt tca gtc ctc tgt ctc cag tat gat gag aga      1023
Leu Thr Gly His Thr Gly Ser Val Leu Cys Leu Gln Tyr Asp Glu Arg
        305                 310                 315 gtg atc ata aca gga tca tcg gat tcc acg gtc aga gtg tgg gat gta      1071
Val Ile Ile Thr Gly Ser Ser Asp Ser Thr Val Arg Val Trp Asp Val
    320                 325                 330 aat aca ggt gaa atg cta aac acg ttg att cac cat tgt gaa gca gtt      1119
Asn Thr Gly Glu Met Leu Asn Thr Leu Ile His His Cys Glu Ala Val
335                 340                 345                 350 ctg cac ttg cgt ttc aat aat ggc atg atg gtg acc tgc tcc aaa gat      1167
```

```
               Leu His Leu Arg Phe Asn Asn Gly Met Met Val Thr Cys Ser Lys Asp
                               355                 360                 365 cgt tcc att gct gta tgg gat atg gcc tcc cca act gac att acc ctc         1215
Arg Ser Ile Ala Val Trp Asp Met Ala Ser Pro Thr Asp Ile Thr Leu
            370                 375                 380 cgg agg gtg ctg gtc gga cac cga gct gct gtc aat gtt gta gac ttt         1263
Arg Arg Val Leu Val Gly His Arg Ala Ala Val Asn Val Val Asp Phe
        385                 390                 395 gat gac aag tac att gtt tct gca tct ggg gat aga act ata aag gta         1311
Asp Asp Lys Tyr Ile Val Ser Ala Ser Gly Asp Arg Thr Ile Lys Val
400                 405                 410 tgg aac aca agt act tgt gaa ttt gta agg acc tta aat gga cac aaa         1359
Trp Asn Thr Ser Thr Cys Glu Phe Val Arg Thr Leu Asn Gly His Lys
415                 420                 425                 430 cga ggc att gcc tgt ttg cag tac agg gac agg ctg gta gtg agt ggc         1407
Arg Gly Ile Ala Cys Leu Gln Tyr Arg Asp Arg Leu Val Val Ser Gly
            435                 440                 445 tca tct gac aac act atc aga tta tgg gac ata gaa tgt ggt gca tgt         1455
Ser Ser Asp Asn Thr Ile Arg Leu Trp Asp Ile Glu Cys Gly Ala Cys
        450                 455                 460 tta cga gtg tta gaa ggc cat gag gaa ttg gtg cgt tgt att cga ttt         1503
Leu Arg Val Leu Glu Gly His Glu Glu Leu Val Arg Cys Ile Arg Phe
    465                 470                 475 gat aac aag agg ata gtc agt ggg gcc tat gat gga aaa att aaa gtg         1551
Asp Asn Lys Arg Ile Val Ser Gly Ala Tyr Asp Gly Lys Ile Lys Val
480                 485                 490 tgg gat ctt gtg gct gct ttg gac ccc cgt gct cct gca ggg aca ctc         1599
Trp Asp Leu Val Ala Ala Leu Asp Pro Arg Ala Pro Ala Gly Thr Leu
495                 500                 505                 510 tgt cta cgg acc ctt gtg gag cat tcc gga aga gtt ttt cga cta cag         1647
Cys Leu Arg Thr Leu Val Glu His Ser Gly Arg Val Phe Arg Leu Gln
            515                 520                 525 ttt gat gaa ttc cag att gtc agt agt tca cat gat gac aca atc ctc         1695
Phe Asp Glu Phe Gln Ile Val Ser Ser Ser His Asp Asp Thr Ile Leu
        530                 535                 540 atc tgg gac ttc cta aat gat cca gct gcc caa gct gaa ccc ccc cgt         1743
Ile Trp Asp Phe Leu Asn Asp Pro Ala Ala Gln Ala Glu Pro Pro Arg
    545                 550                 555 tcc cct tct cga aca tac acc tac atc tcc aga taaataacca tacactgacc      1796
Ser Pro Ser Arg Thr Tyr Thr Tyr Ile Ser Arg
560                 565 tcatacttgc ccaggaccca ttaaagttgc ggtatttaac gtatctgcca ataccaggat      1856
gagcaacaac agtaacaatc aaactactgc ccagtttccc tggactagcc gaggagcagg      1916
gctttgagac tcctgttggg acacagttgg tctgcagtcg gcccaggacg gtctactcag      1976
cacaactgac tgcttcagtg ctgctatcag aagatgtctt ctatcaattg tgaatgattg      2036
gaacttttaa acctccccctc ctctcctcct ttcacctctg cacctagttt tttcccattg     2096
gttccagaca aaggtgactt ataaatatat ttagtgtttt gccagaaaaa aaaa            2151

<210> SEQ ID NO 2
<211> LENGTH: 569
<212> TYPE: PRT
<213> ORGANISM: Artificial sequence
<220> FEATURE:
<223> OTHER INFORMATION: Description of the artificial sequence : cDNA
      coding for human beta-TrCP protein

<400> SEQUENCE: 2

Met Asp Pro Ala Glu Ala Val Leu Gln Glu Lys Ala Leu Lys Phe Met
```

-continued

```
  1               5                    10                   15
Asn Ser Ser Glu Arg Glu Asp Cys Asn Asn Gly Glu Pro Pro Arg Lys
            20                  25                  30

Ile Ile Pro Glu Lys Asn Ser Leu Arg Gln Thr Tyr Asn Ser Cys Ala
            35                  40                  45

Arg Leu Cys Leu Asn Gln Glu Thr Val Cys Leu Ala Ser Thr Ala Met
        50                  55                  60

Lys Thr Glu Asn Cys Val Ala Lys Thr Lys Leu Ala Asn Gly Thr Ser
65                  70                  75                  80

Ser Met Ile Val Pro Lys Gln Arg Lys Leu Ser Ala Ser Tyr Glu Lys
                85                  90                  95

Glu Lys Glu Leu Cys Val Lys Tyr Phe Glu Gln Trp Ser Glu Ser Asp
            100                 105                 110

Gln Val Glu Phe Val Glu His Leu Ile Ser Gln Met Cys His Tyr Gln
            115                 120                 125

His Gly His Ile Asn Ser Tyr Leu Lys Pro Met Leu Gln Arg Asp Phe
130                 135                 140

Ile Thr Ala Leu Pro Ala Arg Gly Leu Asp His Ile Ala Glu Asn Ile
145                 150                 155                 160

Leu Ser Tyr Leu Asp Ala Lys Ser Leu Cys Ala Ala Glu Leu Val Cys
                165                 170                 175

Lys Glu Trp Tyr Arg Val Thr Ser Asp Gly Met Leu Trp Lys Lys Leu
                180                 185                 190

Ile Glu Arg Met Val Arg Thr Asp Ser Leu Trp Arg Gly Leu Ala Glu
            195                 200                 205

Arg Arg Gly Trp Gly Gln Tyr Leu Phe Lys Asn Lys Pro Pro Asp Gly
210                 215                 220

Asn Ala Pro Asn Ser Phe Tyr Arg Ala Leu Tyr Pro Lys Ile Ile
225                 230                 235                 240

Gln Asp Ile Glu Thr Ile Glu Ser Asn Trp Arg Cys Gly Arg His Ser
            245                 250                 255

Leu Gln Arg Ile His Cys Arg Ser Glu Thr Ser Lys Gly Val Tyr Cys
            260                 265                 270

Leu Gln Tyr Asp Asp Gln Lys Ile Val Ser Gly Leu Arg Asp Asn Thr
        275                 280                 285

Ile Lys Ile Trp Asp Lys Asn Thr Leu Glu Cys Lys Arg Ile Leu Thr
290                 295                 300

Gly His Thr Gly Ser Val Leu Cys Leu Gln Tyr Asp Glu Arg Val Ile
305                 310                 315                 320

Ile Thr Gly Ser Ser Asp Ser Thr Val Arg Val Trp Asp Val Asn Thr
                325                 330                 335

Gly Glu Met Leu Asn Thr Leu Ile His His Cys Glu Ala Val Leu His
            340                 345                 350

Leu Arg Phe Asn Asn Gly Met Met Val Thr Cys Ser Lys Asp Arg Ser
        355                 360                 365

Ile Ala Val Trp Asp Met Ala Ser Pro Thr Asp Ile Thr Leu Arg Arg
        370                 375                 380

Val Leu Val Gly His Arg Ala Ala Val Asn Val Val Asp Phe Asp Asp
385                 390                 395                 400

Lys Tyr Ile Val Ser Ala Ser Gly Asp Arg Thr Ile Lys Val Trp Asn
                405                 410                 415

Thr Ser Thr Cys Glu Phe Val Arg Thr Leu Asn Gly His Lys Arg Gly
            420                 425                 430
```

```
Ile Ala Cys Leu Gln Tyr Arg Asp Arg Leu Val Val Ser Gly Ser Ser
        435                 440                 445

Asp Asn Thr Ile Arg Leu Trp Asp Ile Glu Cys Gly Ala Cys Leu Arg
    450                 455                 460

Val Leu Glu Gly His Glu Glu Leu Val Arg Cys Ile Arg Phe Asp Asn
465                 470                 475                 480

Lys Arg Ile Val Ser Gly Ala Tyr Asp Gly Lys Ile Lys Val Trp Asp
                485                 490                 495

Leu Val Ala Ala Leu Asp Pro Arg Ala Pro Ala Gly Thr Leu Cys Leu
            500                 505                 510

Arg Thr Leu Val Glu His Ser Gly Arg Val Phe Arg Leu Gln Phe Asp
        515                 520                 525

Glu Phe Gln Ile Val Ser Ser Ser His Asp Asp Thr Ile Leu Ile Trp
    530                 535                 540

Asp Phe Leu Asn Asp Pro Ala Ala Gln Ala Glu Pro Pro Arg Ser Pro
545                 550                 555                 560

Ser Arg Thr Tyr Thr Tyr Ile Ser Arg
                565
```

<210> SEQ ID NO 3
<211> LENGTH: 19
<212> TYPE: DNA
<213> ORGANISM: Artificial sequence
<220> FEATURE:
<223> OTHER INFORMATION: Description of the artificial sequence : sense
      primer

<400> SEQUENCE: 3
ccaaactgcg tataacgcg                                                    19

<210> SEQ ID NO 4
<211> LENGTH: 20
<212> TYPE: DNA
<213> ORGANISM: Artificial sequence
<220> FEATURE:
<223> OTHER INFORMATION: Description of the artificial sequence :
      antisense primer

<400> SEQUENCE: 4
ggtgaatcaa cgtgtttagc                                                   20

<210> SEQ ID NO 5
<211> LENGTH: 20
<212> TYPE: DNA
<213> ORGANISM: Artificial sequence
<220> FEATURE:
<223> OTHER INFORMATION: Description of the artificial sequence : sense
      primer

<400> SEQUENCE: 5
ggatgatgta taactatc                                                     20

<210> SEQ ID NO 6
<211> LENGTH: 25
<212> TYPE: DNA
<213> ORGANISM: Artificial sequence
<220> FEATURE:
<223> OTHER INFORMATION: Description of the artificial sequence :
      antisense primer

<400> SEQUENCE: 6
tttatcccag atcttgattg tgttg                                             25

```
<210> SEQ ID NO 7
<211> LENGTH: 30
<212> TYPE: DNA
<213> ORGANISM: Artificial sequence
<220> FEATURE:
<223> OTHER INFORMATION: Description of the artificial sequence : primer

<400> SEQUENCE: 7
ccaggatcct tatacaacat tgacagcagc                                          30

<210> SEQ ID NO 8
<211> LENGTH: 29
<212> TYPE: DNA
<213> ORGANISM: Artificial sequence
<220> FEATURE:
<223> OTHER INFORMATION: Description of the artificial sequence : primer

<400> SEQUENCE: 8
ccaggatcct tagtcccaga tgaggattg                                           29

<210> SEQ ID NO 9
<211> LENGTH: 6
<212> TYPE: PRT
<213> ORGANISM: Unknown organism
<220> FEATURE:
<221> NAME/KEY: Variant
<222> LOCATION: 4 - 5
<223> OTHER INFORMATION: Xaa is any natural amino acid
<220> FEATURE:
<221> NAME/KEY: Phosphorylation
<222> LOCATION: 2 and 6
<223> OTHER INFORMATION: Serines are phosphorylated
<220> FEATURE:
<223> OTHER INFORMATION: Description of artificial sequence, consensus
      sequence

<400> SEQUENCE: 9

Asp Ser Gly Xaa Xaa Ser
```

HUMAN βTRCP PROTEIN

The present invention relates to a novel human protein which is involved in the targeting of proteins towards proteasome degradation pathways. This protein, called h-βTrCP, is capable of interacting notably with the Vpu protein of HIV-1 virus and with the cell proteins IκB, β-catenin and Skp1p.

The degradation of proteins by proteasome, a multiprotein complex present in all cells, is involved in numerous essential cell phenomena such as the control of cell proliferation, the renewal of proteins and the removal of incorrectly folded proteins, particularly in the endoplasmic reticulum (CIECHANOVER A., Cell, 79, 13–21,1994). Numerous viruses, like HIV-1 virus, which degrades CD4 via one of its proteins Vpu (MRONO D., Cell, 82, 189–1992, 1995), exploit these cell pathways of protein degradation, in which the proteins are targeted towards proteasome by various interactions with other proteins before being degraded. To be targeted towards and degraded by proteasome, the proteins must generally be ubiquitinylated beforehand by ubiquitin-ligase complexes. Furthermore, to be ubiquitinylated, the proteins must often undergo modifications such as phosphorylations (CIECHANOVER A., Embo. J., 17, 7151–7160, 1998).

Several other proteins of the βTrCP type are known at the present time.

the βTrCP protein of Xenope, described by Spevak et al. (Mol. Cell. Biol., 13, 4953–4966, 1993);

the Slimb protein of drosophila, described by Jiang et al. Nature, vol. 391, Jan. 29, 1998); and the KIAA 0696 protein identified by Ishikawa et al. (DNA Research, 5, 169–176, 1998) during a systematic analysis of sequences expressed in the brain.

Jiang et al. showed that the Slimb protein of drosophila is involved in the stability of the Armadillo protein and the signaling of two metabolic pathways essential for development, namely the Hedgehog and Wingless pathways. They also showed that the Slimb protein has a homology of about 80% with the βTrCP protein of Xenope, none of whose functions was described by Spevak et al. As the β-catenin of Xenope or man, which is the homolog of the Armadillo protein of drosophila, seems to be targeted towards proteasome degradation pathways in the absence of signaling of the Hedgehog and Wingless pathways, said authors suggest that, in man, the genes coding for the homologs of Slimb could be involved in the proteolytic degradation of β-catenin, a protein which acquires oncogenic properties when it is not degraded (POLAKIS P., Biochim. Biophys. Acta, 1332, F127–47, 1997).

However, despite the fact that conservation of the Wingless and Hedgehog pathways in vertebrates is important, it is not certain that the functions of the homologous proteins will be totally conserved. Moreover, there are numerous examples which show that there are always significant differences between species.

Also, solely on the basis of genetic studies, Jiang et al,. established the involvement of Slimb in the control of the Wingless and Hedgehog pathways in drosophila. Proof that this control is dependent on a direct interaction between Slimb and Armadillo, for example, has neither been sought nor found.

The protein according to the invention, called h-βTrCP, is capable of interacting with virus proteins or cell proteins which can act as mediators or be degraded by proteasome. In particular, the h-βTrCP protein is capable of interacting notably with the Vpu protein of HIV-1 virus and with the cell proteins IκB and β-catenin.

It is particularly useful for screening therapeutic agents such as, in particular, antitumoral, antiviral, anti-inflammatory and anti-Alzheimer agents.

The Vpu protein is a small membrane protein of 81 amino acids which is expressed by the majority of isolates of HIV-1 virus but not by those of the considerably less pathogenic FUV-2 virus or by those of SIV simian virus (COHEN et al., Nature, 334, 532–534, 1988, and STREBEL et al., Science, 2, 1221–1223, 1988).

One of the functions of the Vpu protein is its capacity to induce degradation of the CD4 protein, a cell receptor of HIV-1 virus, so it participates in reducing the expression of the CD4 receptor on the cell surface (Willey et al., J. Virol., 68, 1207–1212, 1994).

It is also known that the two phosphorylation serines of the Vpu protein, located in positions 52 and 56, are essential for the degradation of CD4 induced by Vpu (MARGOTIN et al., Virology, 223, 381–386, 1996). Moreover, during the process of infection by HIV-1 in the absence of the Vpu protein, the Gp160 envelope precursor and the newly synthesized CD4 protein combine in the endoplasmic reticulum to block the maturation of the Gp160 protein (BOUR et al., J. Virol., 65, 6387–6396, 1991. Degradation of the CD4 receptor mediated by the Vpu protein is essential for releasing the viral envelope protein which is held in the endoplasmic reticulum by being bound to CD4 through interaction with the Gp120 subunit, and for allowing the normal maturation of the envelope into the plasmic membrane and subsequently its integration into the virus particles, rendering them infectious. Recent studies have demonstrated the fact that degradation of the CD4 receptor mediated by the Vpu protein is sensitive to specific proteasome inhibitors and is dependent on the presence of an "intact ubiquitinylation machinery" (FUJITA et al., J. Gen. Virol., 78, 619–625, 1997).

Thus the Vpu protein participates in absolutely critical functions for assuring the production of large numbers of infectious virus particles, since it acts not only on the products of the gag gene, i.e. on the structural proteins, to increase the release of the virus particles, but also on the products of the env gene to allow the maturation of the envelope protein following degradation of the CD4 receptor. In 1996, MARGOTTIN et al. (supra) showed that the interaction between Vpu and CD4 took place via their cytoplasmic domain and that this interaction was not sufficient to trigger degradation of the CD4 receptor.

The Skp1p protein is a cell protein involved in the targeting of proteins towards proteasome degradation pathways, which depends on the ubiquitinylation of the proteins (PICKART C. M., The Faseb Journal, 11, 1055–1066,1997).

BAI et al. (Cell, 86, 263274, 1996) showed that the Skp1p protein was necessary for ubiquitin-mediated proteolysis and that this degradation took place due to the interaction of Skp1p with proteins containing a unit called F-box.

The Skp1p protein is an essential factor in the targeting of cell cycle regulatory proteins by proteasome. Targeting of the degradation of these regulators is particularly necessary when the cell cycle enters the S phase of DNA synthesis (PAGANO M., The Faseb Journal, 11, 1068–1075, 1997). Recent studies showed that the Skp1p protein and F-box proteins are the essential elements of high-molecular complexes called SCF (Skp1p-Cullin-F-box-protein complexes). These SCF complexes play the role of enzyme E3; through their ubiquitin-ligase activity, they allow the last step of the ubiquitinylation of substrate proteins, which are thus targeted towards degradation by proteasome (HOYT A., Cell, 91, 149–151, 1997). It is further pointed out that no Skp1p homolog has yet been identified in drosophila.

The IκB protein, which exists in different forms (α, β, ε), is the major inhibitor of the NFκB transcription factor, keeping it in the form of an inactive complex in the cytoplasm (Beg A. et al., Genes and Dev., 7, 2064–2070, 1993). After stimulation of the cells by factors such as interleukin-1 (IL1) and tumor necrosis factor (TNF), the IκB protein is phosphorylated on serine residues S32 and S36. This phosphorylation leads very rapidly to the ubiquitinylation of the protein and to the targeting thereof towards degradation by proteasome. The active NFκB factor, for example in the form of two subunits P50 and P65, is then released and imported into the nucleus, where it will be able to activate a very large number of genes and cause inflammatory phenomena in particular.

The β-catenin protein is a cell protein controling the essential signal transduction pathways such as the Wingless pathways, which are very highly conserved in all vertebrates (MILLER et al., Genes and Dev., 10, 2527–2539, 1996, and POLAKIS P., Biochim. Biophys. Acta, 1332, F 127–47, 1997). β-Catenin accumulates in cancerous cells, either as a result of mutations which prevent phosphorylation on serine residues 33 and 37 (mutated β-catenin proteins), or as a result of mutations of its cofactor, the APC protein, which is necessary for its degradation.

The accumulation of β-catenin due to its non-degradation leads to its importation into the nucleus and to the activation of genes controlled by TCF-LEF promoters, causing cell proliferation and transformation phenomena.

It was recently shown that mutations of presenilin-1 in patients suffering from Alzheimer's disease caused a destabilization and enhanced degradation of β-catenin (ZHANG et al., Nature, 395, 699–702, 1998). These authors showed that non-mutated presenilin-1 binds to β-catenin and thereby contributes to its stability. In Alzheimer's disease, the mutated presenilin is no longer capable of binding to β-catenin, so the latter is degraded more rapidly. The level of β-catenin is considerably reduced in the neuronal cells of patients suffering from Alzheimer's disease. The loss of β-catenin causes an enhanced apoptosis of the neuronal cells, which would account for the neuronal loss observed in this pathological condition.

It is easy to see that there is an urgent need for means of modulating, namely activating or inhibiting, the targeting of proteins towards proteasome.

A novel human protein involved in the targeting of proteins towards proteasome degradation pathways has now been found which makes it possible to screen modulators of the targeting of proteins towards proteasome.

The present invention therefore relates to a novel human protein, called h-βTrCP, which has SEQ ID No. 2 and which is involved in the targeting of proteins towards proteasome degradation pathways.

The h-βTrCP protein possesses 569 amino acids and comprises one F-box and seven WD units having the following positions in the sequence SEQ ID No. 2:

| | |
|---|---|
| F-box: | amino acids 147–191, |
| first WD unit: | amino acids 259–292, |
| second WD unit: | amino acids 304–332, |
| third WD unit: | amino acids 343–372, |
| fourth WD unit: | amino acids 387–415, |
| fifth WD unit: | amino acids 427–455, |
| sixth WD unit: | amino acids 467–492, |
| seventh WD unit: | amino acids 516–544. |

Because of the homology of this novel protein with the βTrCP of Xenope, a protein containing 0-transducin units and known as "beta transducin repeats containing protein", the protein of the invention is called h-β-ATrCP (human βTrCP).

Via its WD units, the h-βTrCp protein of the invention is capable of interacting with proteins degradable by proteasome, particularly with virus proteins and cell proteins which possess the phosphorylation unit comprising the amino acids Asp-Ser-Gly-Xaa-Xaa-Ser (SEQ ID NO: 9), in which Xaa is any natural amino acid and in which the serine residues are phosphorylated.

The phosphorylation of this unit Asp-Ser-Gly-Xaa-Xaa-Ser (SEQ ID NO: 9) is essential to the ubiquitinylation and subsequent degradation of proteins possessing this type of unit. The h-βTrCP protein is only capable of interacting with proteins containing this unit when the two serine residues are phosphorylated, and it cannot interact with proteins containing a phosphorylation unit in which the serine residues are mutated to non-phosphorylatable amino acids. By interacting with the phosphorylated proteins on this unit, the h-βTrCP protein controls their ubiquitinylation and their screening towards degradation by proteasome.

The virus protein Vpu and the cell proteins IκB and β-catenin may be mentioned in particular among these proteins.

It has also been found that the h-βTrCP protein interacts via its F-box with the Skp1p protein, so it forms part of a novel SCF complex, SCF-h-βTrCP, which selects certain cell or virus proteins for degradation by proteasome. Through its activity of targeting towards proteasome degradation pathways, the h-βTrCP protein according to the invention acts as cell mediator of the Vpu protein in cells infected with HIV-1 virus.

Without wishing to exclude other theories, it is thought that, in cells infected with HIV-1 virus, the virus uses, via the Vpu protein, the SCF complex (of which the βTrCP protein forms part) to induce degradation of the CD4 receptor, which will favor the replication of the virus and the release of the infectious virions.

The invention further relates to the peptide fragments of the h-βTrCP protein which result from the addition, deletion and/or replacement of one or more amino acids, said peptide fragments having conserved the activity of interacting with proteins degradable by proteasome, particularly with the Vpu protein of HIV-1 virus, with the cell protein IκB or the cell protein β-catenin and/or with the Skp1p protein.

The invention relates in particular to the peptide fragments which comprise at least one of the following amino acid sequences of h-βTrCP:

251–569,

292–569,

292–396,

292–545 and

1–291.

Very particularly preferred peptide fragments are those which are partially or totally devoid of the F-box or those which are partially or totally devoid of the WD units.

One particularly preferred peptide fragment is the mutant with residues 32–179 deleted, which is hereafter called βTCPΔF.

The present invention further relates to the nucleic acid sequences, namely the genomic DNA sequences and the cDNA or mRNA sequences, which comprise or consist of a concatenation of nucleotides coding for the h-βTrCP protein or for any one of its peptide fragments as defined above.

The invention relates notably to those nucleic acid sequences coding for the h-βTrCP protein and its peptide fragments described above which are represented by:

a) the cDNA sequence SEQ ID No. 1 coding for said h-βTrCP protein and the cDNA sequences of the nucleic acid fragments coding for said peptide fragments;

b) the DNA sequences which hybridize with the above sequences under strict conditions;

c) the DNA sequences which, due to the degeneracy of the genetic code, result from the sequences a) and b) above and code for the h-βTrCP protein or its fragments; and d) the corresponding mRNA and DNA sequences.

The proteins and peptide fragments according to the invention can be obtained by the genetic engineering technique comprising the following steps:

culture of a microorganism or eukaryotic cells which have been transformed with the aid of a nucleic acid sequence according to the invention; and recovery of the protein or the peptide fragment produced by said microorganism or said eukaryotic cells.

This technique is well known to those skilled in the art. Further details on this subject may be obtained by reference to the following work: Recombinant DNA Technology 1, Editors Ales Prokop, Raskesh K. Bajpai; Annals of the New York Academy of Sciences, volume 646, 1991.

They can also be prepared by the conventional peptide syntheses well known to those skilled in the art.

The nucleic acids according to the invention can be prepared by chemical synthesis and genetic engineering using the techniques well known to those skilled in the art, as described e.g. by SAMBROOK et al. (supra).

For example, the cDNA sequences according to the invention can be synthesized by amplifying the mRNAs of human cells by the PCR (Polymerase Chain Reaction) method, as described e.g. by GOBLET et al. (Nucleic Acid Research, 17, 2144, 1989), using, as primers, synthetic oligonucleotides defined from the DNA sequence SEQ ID No. 1.

The amplified nucleic acid fragment can then be cloned by the techniques described by AU SUBEL et al. (Current Protocols in Molecular Biology, chapter 3, supra).

The invention further relates to transgenic animals which express a transgene for the h-βTrCP protein of the invention, or transgenic animals in which the βTrCP gene has been invalidated.

These transgenic animals or animals in which the h-βTrCP protein gene has been invalidated may be used as models for the in vivo study of perturbation of the cell cycle and proliferation by the absence or overexpression of the gene for the h-βTrCP protein or for truncated or mutated forms of this protein, the Skp1p protein, the Vpu protein, the IκB protein or the β-catenin protein.

These transgenic animals are obtained by techniques well known to those skilled in the art, such as those described in Manipulating the mouse embryo; a laboratory manual. HOGAN B., BEDDINGTON R., COSTANNNI F. & LACY E., Cold Spring Harbor laboratory press, second edition, 1994.

The preferred animals are mammals such as mice or rats.

The invention further relates to the prokaryotic microorganisms and eukaryotic cells transformed with the aid of an expression vector containing a DNA sequence according to the invention. This expression vector, which can be e.g. in the form of a plasmid, must contain, in addition to the DNA sequence of the invention, the means necessary for its expression, such as, in particular, a promoter, a transcription terminator, an origin of replication and, preferably, a selection marker. The transformation of microorganisms and eukaryotic cells is a technique well known to those skilled in the art, who will easily be able to determine, as a function of the microorganism to be transformed, the means necessary for the expression of the DNA sequence according to the invention.

The preferred microorganism for the purposes of the invention is *E. coli,* while the yeast used is preferably *Saccharomyces cerevisiae.*

COS, CHO, SF9, Jurkat and other cells, all of which are listed in the ATCC, may be mentioned in particular as examples of eukaryotic cells which are suitable for the purposes of the invention.

The invention further relates to the eukaryotic cells cotransformed with expression vectors containing on the one hand the DNA sequence coding for the Vpu protein, for the Skp1p protein, for the IκB protein or for the mutated β-catenin proteins, and on the other hand a sequence coding for the h-βTrCP protein, said expression vectors also containing means useful for their expression, including in the yeast two-hybrid system.

The present invention therefore further relates to the anti-HIV-1 antiviral agents consisting of the peptide fragments of the h-βTrCP protein of the invention which have conserved the properties of interaction of the h-βTrCP protein either with the Vpu protein or with the Skp1p protein. These peptide fragments are devoid of the F-box or the WD units, so they are no longer able to interact with the Skp1p protein or, respectively, the Vpu protein.

Other antiviral agents, antitumoral agents or anti-inflammatory agents which may be mentioned are antibodies directed against the h-βTrCP protein of the invention and its peptide fragments, said antibodies being a further subject of the invention.

These antibodies can be monoclonal antibodies obtained by the well-known method of KOHLER and MILSTEIN (Nature, 256, 495–497, 1975) or polyclonal antibodies obtained by the conventional methods of animal immunization (Antibodies, a laboratory manual. E. Harlow & D. Lane. Cold Spring Harbor laboratory press, 1988).

Finally, antiviral agents, antitumoral agents or anti-inflammatory agents which may be mentioned are antisense oligonucleotides which block the transcription or translation of the h-βTrCP protein of the invention and which hybridize with a nucleic acid sequence as defined above, said oligonucleotides also forming a further subject of the present invention.

These antisense oligonucleotides are prepared by techniques well known to those skilled in the art, such as those described by AUSUBEL et al. (Current Protocols in Molecular Biology, Green Publishing Associates and Wiley-Interscience, New York, 1989, published up to 1997).

The peptide fragments of h-βTrCP which possess the F-box or which have conserved both the WD units and the F-box can be used as antitumoral or anti-inflammatory agents.

The peptide fragments of h-βTrCP which are devoid of the F-box can be used in gene therapy for the treatment of osteoarticular inflammatory diseases or acute inflammatory syndromes which are accompanied by NFκB activation induced by the massive release of TNFα during these processes.

As illustrated in FIG. 7, the expression of h-βTrCPΔF is capable of massively inhibiting, by a factor of about 20, the transcription activation induced by TNFα. Therefore, h-βTrCPΔF could act as a potent anti-inflammatory agent in any pathological condition associated with an intense inflammatory reaction due to a release of TNFα. For example, several attempts are currently being made to apply gene therapy to rheumatoid polyarteritis by injecting recombinant viruses into the damaged joints. Vectors expressing h-βTrCPΔF can be used in these gene therapy experiments on inflammatory syndromes. These vectors may be of several types (retroviruses, adenoviruses; ANDERSON F., Nature, 392, 25–30, 1998). The expression of h-βTrCPΔF may be monitored by its effects on the inhibition of NFκB activation by TNF.

The present invention further relates to the use of the h-βTrCP protein, or the nucleic acid sequences coding for this protein or for its peptide fragments, for the screening of therapeutic agents which are capable of modulating the interaction of the h-βTrCP protein with proteins degradable by proteasome, and particularly for the screening of:

- anti-HIV-1 antiviral agents capable of inhibiting the interaction between the h-TrCP protein and the Vpu protein and/or inhibiting the interaction between the h-βTrCP protein and the Skp1p protein;
- antitumoral agents capable of perturbing the regulation of the cell cycle or the protein degradation processes in tumoral human cells by modulating (inhibiting or activating) the interaction between the h-βTrCP protein and the Skp1p protein, and by reactivating the interaction between the h-βTrCP protein and the mutated β-catenin proteins in tumoral cells, or between the TrCp protein and the normal β-catenin protein in tumoral cells devoid of the APC protein;
- anti-inflammatory agents capable of perturbing the activation of the NFκB transcription factor by inhibiting the interaction between the h-βTrCP protein and the IκB protein; and
- anti-Alzheimer agents capable of reducing the degree of degradation of β-catenin in neuronal cells by inhibiting the interaction between the h-βTrCP protein and the β-catenin protein.

In fact, by perturbing the Vpu/h-βTrCP and/or Skp1p/h-βTrCP interactions, it is possible:

- either to inhibit the replication and production of HIV-1 virus by infected cells;
- or to inhibit the entry of the cell cycle into the S phase and to have an antiproliferative effect.

By perturbing the IκB/h-βTrCP and/or Skp1p/h-βTrCP interactions, it is possible to inhibit the degradation of the IκB protein by proteasome and hence to inhibit the activation of the NFκB transcription factor.

Finally, by activating the mutated β-catenin/h-βTrCP interaction, it is possible to activate the degradation of the β-catenin which has accumulated in tumoral cells. By inhibiting the β-catenin/h-βTrCP interaction in patients suffering from Alzheimer's disease, it is possible to reduce the apoptosis of neuronal cells.

Screening of Modulators of the h-βTrCP/Protein Interaction

The antiviral agents can be selected either from random peptide banks on the surface of phages (SCOTT J. et al., Science, 249, 386–390, 1990) or by using random synthetic oligonucleotides according to the technique of the SELEX type (TUERK and GOLD, Science, 249, 505–510, 1990). This technique makes it possible to isolate, from a very large pool of oligonucleotides, those which have a high affinity for the protein of interest, namely the h-βTrCP protein in the present case. They are called aptamers. From these aptamers it will be possible, using the screening method below, to select those which inhibit both the Vpu/h-βTrCP and Skp1p/h-βTrCP interactions.

The screening method defined above can be carried out e.g. by using the yeast two-hybrid system in which yeast cells co-expressing the h-βTrCP protein according to the invention and one of the proteins Vpu, IκB, β-catenin or Skp1p are cultivated on appropriate selective media in the presence of the test substance; the selective media are the media commonly used in this field and hence are well known to those skilled in the art.

The yeast two-hybrid system is described by FIELDS and SONG in Nature, 340, 245–246, 1989, and in patent U.S. Pat. No. 5,667,973. This two-hybrid system is based on detection of the protein-protein interactions by activation of the His or LacZ reporter gene under the control of Gal4 transcription activation domains in the yeast.

In this two-hybrid system, a yeast is cotransformed with a two-hybrid vector containing the cDNA of one of the proteins and a vector containing the cDNA of the other protein, each of said vectors containing either a DNA binding domain or a transcription activation domain. The two proteins are then expressed by the yeast in an appropriate culture medium, for example a histidine-free culture medium. The interaction between the two hybrid proteins allows on the one hand activation of the His3 gene and growth of the yeasts on a histidine-free medium, as well as activation of the LacZ gene, which is disclosed by a color reaction specific for β-galactosidase. It is therefore possible to verify the interaction when the yeasts grow on a histidine-free medium and when a color reaction is observed.

A further possibility is to use the halo test as described by Valtz & Peter (Meth. Enzymol., 283, 350–365, 1997) to detect whether there is any interaction.

It is also possible to use variants of the two-hybrid system, such as the three-hybrid system described by TIRODE et al. (J. Biol. Chem., 272, 22995–22999, 1997) or by COLAS et al. (Nature, 380, 548–550, 1996), in which a peptide inhibiting the interaction can be expressed as a third partner to inhibit the interaction of the other two. A random peptide bank can also be used in this way.

A further possibility is to use the reverse-hybrid system described by VIDAL et al. (Proc. Natl. Acad. Sci., 93, 10315–10320), in which selection is carried out against an interaction and not for an interaction. In this system, as in the conventional two-hybrid system, it is possible to screen banks of small chemical molecules, including those derived from chemical synthesis, in order to bring yeasts cotransformed with two-hybrid or reverse-hybrid vectors carrying fusions with the Vpu protein, the IκB protein, β-catenin, the h-βTrCP protein or the Skp1p protein into contact with these small molecules in the search for an inhibitor of the Vpu/h-βTrCP, Skp1p/h-βTrCP, β-catenin/h-βTrCP or IκB/h-βTrCP interactions.

The screening assays for interaction inhibitors may also be carried out using the conjugative two-hybrid system (FROMONT-RACINE et al., Nature Genetics, 16, 277–282, 1997), the membrane two-hybrid system (BRODER Y. C. et al., Curr. Biol., 8, 1121–1124, 1998) and optionally, if phosphorylations can take place in the bacteria, the bacterial two-hybrid system (KARIMOVA et al., Proc. Natl. Acad. Sci., 95, 5752–5756, 1998).

This screening can also be effected in vitro by using one of the proteins Vpu, IκB, β-catenin or Skp1p and the h-βTrCP protein, one of the proteins being immobilized on an appropriate support and the other being labeled by any means used in the methods of detecting biological substances, it being possible for this labeling means to be e.g. a radioactive isotope, a luminescent agent, biotin or a specific antibody.

One of the proteins will preferably be immobilized in the form of a fusion protein with glutathione S-transferase (GST) on agarose-glutathione beads or in microtiter plates, the GST serving as an agent for coupling said protein with the beads or with the wells of the plates.

This can be done particularly using the scintillation proximity assay (SPA) described by BOSWORTH et al. (Nature, 341, 167–168, 1989) and marketed by Amersham. This assay consists in labeling one of the proteins with a radioactive element, for example tritium, and immobilizing the other protein on magnetic beads or agarose-glutathione beads. The inhibitory effect of the test substances on interactions involving the h-βTrCP protein can easily be detected, without separation of the bound or free radioactive species, according to the protocols described by BOSWORTH et al. (supra).

Another possible technique is that of surface plasmon resonances described by KARLSSON et al. (J. Immunol. Methods, 145, 229–233, 1991), using Biacore, marketed by Pharmacia, to isolate the inhibitors of interactions involving the h-βTrCP protein according to the invention.

The inhibitory activity of the antiviral agents selected in this way may be verified by assays on $CD_4$+T cells or on chimpanzees infected with HIV-1 virus or SIV Cpz.

The antitumoral agents and anti-inflammatory agents—ligands of the h-βTrCP protein of the invention—can also be isolated by the two-hybrid techniques or related techniques or by interaction in vitro with combinatorial banks of peptides or other chemical products, as described above.

The specificity of the antiviral, antitumoral or anti-inflammatory agents selected by the two-hybrid assay can then be determined by the culture of mammalian cells, for example human cells transfected with the βTrCp protein or a fragment thereof, in the presence of a reporter gene specific for the protein involved in the pathological condition which it is desired to treat.

Thus, for the IκB protein, it will be possible to use human cells originating from the cell lines Hela, 293, 293T, etc. and the reporter gene dependent on NFκB sites (3Enh-κB-ConA Luc), which controls the expression of luciferase.

In non-stimulated human cells, the human βTrCP protein is transitorily expressed from a eukaryotic expression vector such as pCDNA3 (Invitrogen), or any other eukaryotic expression vector, which has inserted the DNA coding for the βTrCP protein under the control of a strong promoter of the cytomegalovirus, CMV, or the like. An amount of the order of 3 μg of this vector permitting the expression of the βTrCP protein will be cotransfected by one of the common transfection techniques (calcium phosphate, lipofectamine (Life Technologies), electroporation (Ausubel and Sambrook, cf. below) etc.) with 1 μg of a reporter vector dependent on NFκB sites (3Enh-κB-ConA luc) or independent of NFκB sites (RSV Luc or ConA Luc) which control the expression of the luciferase reporter gene. Molecules capable of inhibiting the h-βTrCP/IκB interaction will inhibit the increase in the expression of lucifersse in this assay. These inhibitors will be added to the culture medium for at least 6 hours, 24, 36 or 48 hours after transfection. The specificity of these inhibitors may be checked by verifying that they have no effect on RSV Luc or ConA Luc. Another possible alternative will be to use the dual luciferase system from Promega, in which two different reporter vectors can be assayed at the same time.

According to one experimental protocol similar to that described above, but with stimulated cells, it will be possible to verify that the inhibition induced by the expression of the h-βTrCPΔF fragment on the TNF-dependent transcription activation has been nullified.

Thus, in this second assay, the human cells are cotransfected with 1 μg of reporter vector, i.e. either 3Enh-κB-ConA Luc, ConA Luc or RSV Luc, and with 3 μg of pCDNA3 expressing the h-βTrCPΔF peptide fragment, which is a mutant of βTrCP with its F-box deleted. 24 to 48 h after transfection, the cells are treated for 6 h with TNF or okadaic acid (OKA), which are potent NFκB activators (BAUERLE et al., Cell, 1996, 87, 13–20). The h-βTrCPΔF mutant has a massive inhibitory effect on the expression of the luciferase reporter compared with a control plasmid transfected under the same conditions. This effect is due to the inhibition of IκB degradation induced by the binding of the h-βTrCPΔF mutant in place of the endogenous wild-type h-βTrCP protein. Therefore an inhibitor of the h-βTrCP/IκB interaction will also inhibit the h-βTrCPΔF/IκB interaction and hence will reverse the inhibitory effect of the h-βTrCPΔF fragment. The potential inhibitors are added to the medium under the same conditions as those indicated above. From the cells stimulated with TNF or OKA, those inhibitors are chosen which induce an increase in the expression of the reporter gene.

After the selection of inhibitors in the previous two assays, a third assay can be carried out to verify that they are capable of inhibiting the activation of NFκB induced by stimulation of the cells with TNF or OKA.

The cells transfected only with 1 ng of reporter vector (3Enh-KB-ConA Luc) and stimulated for 6 h with TNF or OKA are treated with the potential inhibitors. To be specific, these inhibitors must have an effect only on the IκB-dependent reporter vectors and not on the other reporter vectors (ConA or RSV).

In the case of β-catenin, it will be possible to use human cells originating from the above lines transformed with mutated β-catenin or the peptide fragment of βTrCP devoid of the F-box, in the presence of vector Top-TK-Luci, which contains a multimer of TCF-LEF sites responding to β-catenin, patenin, or Fop-tk Luci, which contains an inactive mutated multimer and no longer responds to β-catenin.

Detection of β-catenin Mutations

Furthermore, as oncogenic mutated β-catenin can easily be distinguished from wild-type β-catenin by the fact that the former, in contrast to the latter, is incapable of binding to βTrCP in the two-hybrid assay, β-catenin mutations can be detected in human tumors by measuring the interaction with βTrCP in the two-hybrid assay.

This assay is valuable because β-catenin mutations are found in numerous cancers such as colon cancer, melanomas, hepatocarcinomas, etc. The only way of detecting these mutations hitherto was to sequence the β-catenin by carrying out RT-PCR on the RNA of the tumors studied. For greater reliability, several double-stranded sequences have to be made in this assay of the prior art. Also, the existence of a mutation does not in itself indicate the oncogenic character of this mutation. It could be a case of polymorphism unconnected with tumorigenicity.

The advantage of the two-hybrid assay with the βTrCP protein is that, in times equivalent to those required to obtain a sequence, it is possible to obtain a clear answer regarding the percentage of oncogenic mutated β-catenin sequences detected from the tumoral RNA. Over a large number of colonies, the percentage of oncogenic forms of β-catenin which are incapable of interacting with βTrCP, compared with the wild-type forms which do interact with βTrCP, can be determined precisely. The assay can be performed in a time equivalent to that required to obtain a few sequences, and at a reduced cost.

This assay comprises the following steps:

1—Preparation of the total RNA from a biopsy of a tumor and of the surrounding healthy tissue, as control, using one of the various RNA preparation techniques or kits (AUSUBEL et al., Current Protocols in Molecular Biology).

2—Amplification of the catenin sequences of the tumor and of the surrounding healthy tissue by carrying out RT-PCR on the RNA samples using a pair of oligonucleotides which permit amplification either of the N-terminal part only (1-130), which contains the most frequently encountered oncogenic mutations (RUBINFELD B. et al., Science, 275, 1790–1792, 1997; DE LA COSTE et al., Proc. Natl. Acad. Sci. USA, 95, 8847–8851, 1998), or of the whole of the β-catenin coding sequence.

3—Insertion of these amplified fragments, by ligation, into one of the two-hybrid vectors, for example pGAD1318, to give a frame fusion with the Gal4 transcription activation domain or the equivalent activation domain for transcription or binding to the DNA coded for by the two-hybrid vector used.

4—ransformation of bacteria of various appropriate strains and plating of the whole of the transformant on LB-ampicillin medium.

5—Harvesting of all the colonies and plasmid minipreparation (AUSUBEL, supra).

6—L40 yeasts or any other appropriate strain of yeast will be cotransformed by the plasmid containing the β-catenin sequences of the above minipreparation with a fusion hybrid containing βTrCP, for example pLexA-βTrCP, in which the βTrCP is fused to the LexA DNA binding domain. A two-hybrid assay is performed on all the colonies obtained, for example by plating the cotransformed yeasts on DO-W-L medium and then transferring the colonies to selective medium for detection of the interactions, i.e. DOW-L-H medium, or in the presence of X-Gal for detection of the interactions by β-galactosidase production (BARTEL P. & FIELDS S., Meth. Enzymol., 254, 241–263, 1995).

This assay requires the following reagents:

1—Vector pGAD1318 predigested at the appropriate sites for inserting the amplified fragment obtained by RT-PCR.

2—The appropriate oligonucleotides for amplifying the β-catenin sequence and then inserting the amplified β-catenin sequences. The oligonucleotide primers for amplification will be chosen according to the mode of insertion of the amplified fragment and the chosen sites.

3—Plasmid pBTM116-βTrCP expressing βTrCP fused to the LexA DNA binding domain.

4—As control, plasmids coding for fusion hybrids with control proteins, for example pLexRas and pGAD1318Raf.

The gap repair technique (SCHWARTZ H. et al., Mutation detection by a two-hybrid assay, Hum. Mol. Gen., 7, 1029–1032, 1998) may also be applied for this assay in order to insert the sequence of the amplified β-catenin fragment into the two-hybrid vector and transform yeasts directly without proceeding via the step of prior transformation in bacteria.

The invention will now be described in detail with the aid of the following account of experiments.

A large part of the techniques described in these Examples, which are well known to those skilled in the art, is explained in detail in the book by SAMBROOK et al. (supra) or in the book by AUSUBEL et al. (supra).

The following description will be understood more clearly with the aid of FIGS. 1 to 12, in which:

FIG. 2 shows the sequences of 4 proteins: h-βTrCP of the invention, βTrCP1 of Xenopus, Met30p of *Saccharomyces cerevisiae* and Scon2p of *Neurospora crassa*;

FIG. 4 is a photograph of a Petri dish showing the growth of yeast cells cotransformed by plasmids containing Skp1p +h-βTrCP; Skp1p +h-βTrCP-Δ7W, Skp1p+VBP1 and Skp1p+$CD4_c$, on medium in the presence of histidine (His+), on medium in the absence of histidine (His−) and on medium in the presence of the β-galactosidase substrate X-Gal (β-Gal);

FIG. 6 is a photograph of a Petri dish showing the growth of yeast cells cotransformed by plasmids containing βTrCP+ IκBα, βTrCP+IκBα S32-36AA, βTrCP+Raf, Ras+IκBα, βTrCP+Vpuc and Ras+Raf, on His+ medium, on His− medium and the expression of β-pal;

EXAMPLE 1

Figure 1:
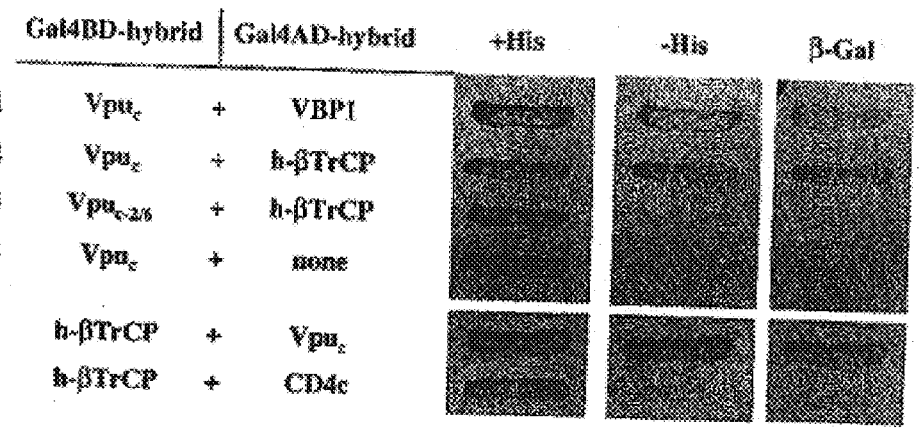
FIG. 1A is a photograph of a Petri dish showing the growth of yeast cells cotransformed by plasmids containing $Vpu_c$+VBP1, $Vpu_c$+h-βTrCP, $Vpu_{c\text{-}2/6}$+h-βTrCP, $Vpu_c$, h-βTrCP+$Vpu_c$ and h-βTrCP+$CD4_c$, on medium in the presence of histidine (His+), on medium in the absence of histidine (His−) and on medium in the presence of the β-galactosidase substrate X-Gal (β-Gal)
FIG. 1B is a photograph of a gel (Northern blot) showing 3 mRNAs of the h-βTrCP protein of the invention.
FIG. 1C is a photograph of an immunoblot showing the expression of the h-βTrCP protein of the invention.
Figure 1:
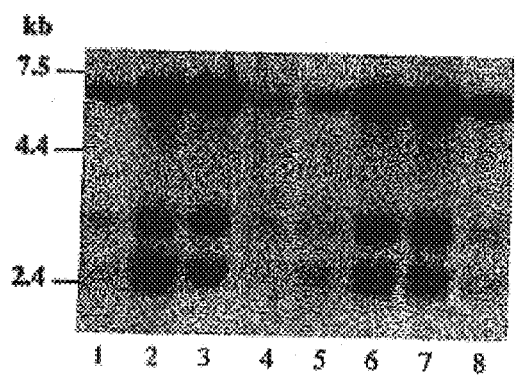
Figure 1:
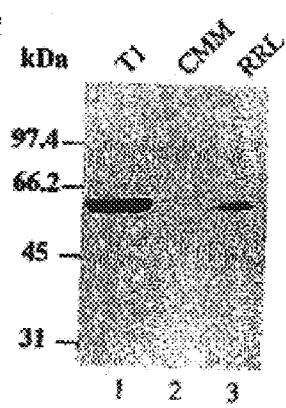

Yeast Two-hybrid Screening/Identification of the cDNA Sequence of the h-βTrCP Protein, and the h-βTrCP protein The chosen target was the cytoplasmic domain of the Vpu protein. Amino acid residues 28 to 81 of the Vpu protein from the IAI isolate of HIV-1 were fused to the Gal4 DNA binding domain (Gal4BD). The cDNA library screened was that of Jurkat cells (human T lymphocyte line, ATCC no. TIB 152) and it was fused to the Gal4 activation domain (Gal4AD) in vector pGAD1318 (BENICHOU et al., J. Biol. Chem., 269, 30073–30076, 1994).

The 1.3 kb clone which was initially isolated by the two-hybrid system (called VBP1) codes for a partial complementary DNA. This partial cDNA codes for a 319 amino acid fragment corresponding to the C-terminal domain of the h-βTrCP protein. It contains seven repeating units followed by a 24 amino acid C-terminal tail. These repeating units, which are known, are called WD units because their end usually terminates in the sequence Trp-Asp (WD). It will be noted that WD units are involved in protein-protein interactions (NEER et al., Nature, 371, 297–300, 1994).

The clone isolated in this way was characterized by DNA sequencing on an Applied Biosystems automated sequencer known as ABI 373A. The DNA sequencing technique is well known to those skilled in the art and is described especially in the book by SAMBROOK et al. entitled "Molecular Cloning: a Laboratory Manual", published by Cold Spring Harbor Press, NY, 1989.

A cDNA library search showed that this clone is homologous with a sequence coding for the βTrCP protein of Xenope, previously identified by SPEVAK et al. (Mol. Cell. Biol., 13, 4953–4966, 1993).

The complete cDNA (2.1 kb) of the h-βTrCP protein, which has SEQ ID No. 1, was obtained by carrying out the polymerase chain reaction (PCR) technique on a plasmid preparation corresponding to the complementary DNA library of Jurkat cells, as defined above, in vector pGAD1318.

In addition to the seven WD units identified in the C-terminal fragment, the whole h-βTrCP protein according to the invention possesses an N-terminal domain of about 250 amino acids. The N-terminal fragment contains a unit for which a consensus sequence has recently been defined by the term F-box and whose role is supposedly to target proteins towards the protein degradation machinery mediated by ubiquitin through the interaction of proteins containing this F-box with the Skp1p protein (BAI et al., 1996, supra).

Thus, via its WD units, the h-βTrCP protein on the one hand is capable of interacting with the Vpu protein and on the other hand possesses an F-box unit which interacts with the Skp1p protein and is therefore capable of targeting proteins towards proteasome degradation pathways.

The h-βTrCP protein possesses 569 amino acids and comprises one F-box and seven WD units having the following positions in the sequence SEQ ID No. 2:

| | |
|---|---|
| F-box: | amino acids 147–191, |
| first WD unit: | amino acids 259–292, |
| second WD unit: | amino acids 304–332, |
| third WD unit: | amino acids 343–372, |
| fourth WD unit: | amino acids 387–415, |
| fifth WD unit: | amino acids 427–455, |
| sixth WD unit: | amino acids 467–492, |
| seventh WD unit: | amino acids 516–544. |

The technique of sequence alignment according to MACAW's program (SCHULER et al., Proteins: structure, function and genetics, 9, 180–190, 1991), a technique well known to those skilled in the art, was used to determine whether the protein isolated in this way had any homology with already known proteins.

Figure 2B:
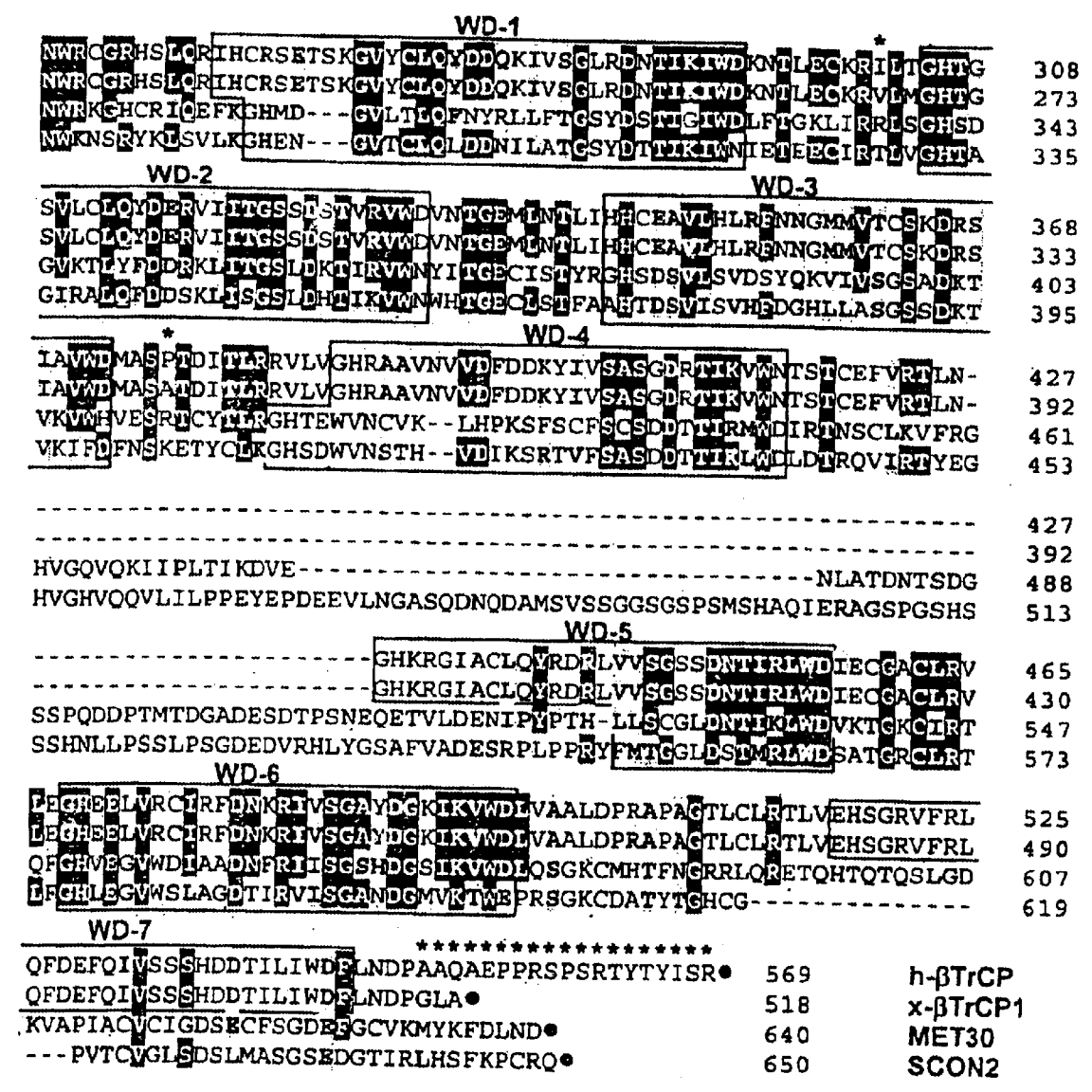

The results obtained are reported in FIG. 2, which shows that the h-βTrCP protein has a homology of:

88% with the x-βrCP1 protein of Xenopus,

33% with the Met30p protein of *Saccharomyces cerevisiae*, a transcription inhibitor involved in biosynthesis, and 31% with the Scon2p protein of *Neurospora crassa*.

FIG. 2 also shows the location of the F-box and the WD units.

EXAMPLE 2

Cloning of the cDNA of the h-βTrCP Protein

The cDNA of the h-βTrCP protein of SEQ ID No. 1 was amplified by carrying out PCR on 2 µg of plasmid DNA from the pGAD cDNA library using two amplification turns, the outer pair of primers for the first turn consisting of the sense primer A of SEQ ID No. 3 (in pGAD1318) and the antisense primer B of SEQ ID NO. 4 (in VBP1) and the inner pair of primers for the second turn consisting of the sense primer C of SEQ ID No. 5 (in pGAD 1318) and the antisense primer D of SEQ ID No. 6 (in VBP1).

Following this procedure, a 1.4 kb fragment, subcloned in plasmid pGAD-VBP1 in the form of a 5'Spe1-3'BglII fragment, was isolated to reconstitute the pGAD-h-βTrCP clone.

The sequences coding for VBP1 (amino acid residues 251 to 569 of the h-βTrCP protein) or coding for the whole h-βTrCP protein were subcloned in vectors pGBT9, pGEX4T2 (Pharmacia) or pCDNA3 (only for the h-βTrCP protein) (Invitrogen) using standard procedures.

EXAMPLE 3

Specific Interaction of the Vpu Protein with the h-βTrCP Protein

The experimental results which demonstrate the specific interaction of the novel human βTrCP protein with the Vpu protein are illustrated in FIG. 1.

3a—Interaction Between the Vpu Protein and the h-βTrCP Protein via the Two-hybrid Screen Described Above FIG. 1A shows the interaction, via the two-hybrid technique, of the C-terminal region of the h-βTrCP protein (VBP1) originating from the cDNA library of Jurkat cells (line 1), or the whole h-βTrCP protein (line 2), fused to the Gal4 activation domain, with the Vpu cytoplasmic domain fused to the Gal4 DNA binding domain, or vice-versa (line 5). The interaction is revealed by activation of the two reporter genes His3 and LacZ; the Hir3 gene permits the growth of yeasts in the absence of histidine (–His panel) and the LacZ gene induces the production of β-galactosidase, revealed by the blue coloration in the presence of the substrate X-Gal (β-Gal panel). This interaction is specific since it is not found between the Vpu protein and the vector alone (line 4) or between the h-βTrCP protein and another protein such as the cytoplasmic region of CD4 (line 6). The +His panel is a control panel showing that all the combinations, including those where there is no interaction, grow in the presence of histidine.

It should be noted that the h-βTrCP protein does not interact with an inactive Vpu protein mutant, Vpuc-2/6 (line 3), a clone mutated on the two scrine residues Ser 52 and Ser 56, which are essential for the activity of Vpu (MARGOTTIN et al., 1996, supra). This result demonstrates that there is a correlation between the capacity of Vpu to interact with h-βTrCP and its activity.

3b—Demonstration of the Expression of the h-βTrCP Protein by Northern Blot Analysis By Northern blot analysis of the mRNAs of different human cell lines using a 5' probe, it was found that several messenger RNAs (mRNAs) hybridize with a probe corresponding to h-βTrCP (FIG. 1B). These mRNAs, of respective sizes 2.4 kb, 3.5 kb and 7 kb, are found in all the human tissues assayed. This multiplicity of mRNAs is reminiscent of the situation described by HUDSON et al. (Dev. Genet., 19, 190–198, 1996) for the mRNAs of the βTrCP of Xenope, for which 3 different mRNAs, with respective sizes similar to those found here for the mRNAs of h-βTrCP, were reported.

3c—Demonstration of the Expression of the h-BTrCP Protein by Immunoblot Analysis Anti-h-βTrCP antipeptide antibodies (Abs) were produced in rabbits by immunization with the synthetic peptide 275–293 corresponding to the first WD unit of the h-βTrCP protein. These Abs were purified by the affinity method by adsorption on 30 μg of the GST-VBP1 fusion protein, which is expressed in E. coli from vector pGEX-VBP1 and immobilized after electroblotting on a nitrocellulose membrane. The purified Abs antibodies were then eluted with the eluent glycine.HCl, pH 3.0, neutralized with 1 M TRIS buffer, pH 8.0, and used for analysis, by the Western blot technique, of the expression of the h-βTrCP protein in human Sup T1 cells (T1), in rabbit reticulocytes (RRL) and in canine microsomal membrane lyzates (CMM).

FIG. 1C shows the expression of the h-βTrCP protein detected in a lyzate of human T cells of the Sup T1 line (line 1) and Promega rabbit reticulocytes (line 3) by the Western blot technique using the previously obtained anti-h-βTrCP antibodies directed against the peptide 275–293. On the other hand, no proteins corresponding to h-βTrCP could be detected in Promega canine pancreatic microsomal membranes (line 2). The size of the h-βTrCP protein detected (60 kD) indicates that the clone of h-βTrCP cDNA, which was characterized and is shown in FIG. 2, is capable of coding for the whole h-βTrCP protein.

EXAMPLE 4

Mapping of the Sites of Interaction Between Vpuc and the h-βTrCP Protein

The sites of interaction between the cytoplasmic domain of the Vpu protein (Vpuc) and the h-βTrCP protein of the invention were determined as follows:

As regards Vpuc, it was shown that mutation of the serines in positions 52 and 56 (Vpuc-2/6 clone) totally eliminated the interaction between Vpu and h-βTrCP.

As regards h-βTrCP, the results of two-hybrid interaction with the Vpu cytoplasmic domain and the different mutants described below show that all the WD units and the C-terminal tail are required for an optimum interaction, as indicated in the Table below.

The following mutants are used:

VBP1ΔW$_1$ (VBB1 clone in which the first WD domain has been deleted; residues 292 to 569. which correspond to a BglII-Xho1 fragment of VBP1);

VBP1-ΔW$_{4-7}$ (VBP1 clone in which WD domains 4 to 7 have been deleted; residues 292 to396); and VBP1-ΔC-ter (VBP1 clone in which the C-terminal tail after the 7th WD domain has been deleted; residues 292 to 545)

by PCR using respectively the sense primer C, described above, and the following antisense primers E and F in VBP1:

primer E: SEQ ID No. 7 primer F: SEQ ID No. 8

The h-βTrCP-Δ7W mutant (h-βTrCP clone in which the seven WD domains have been deleted; residues 1 to 291) was constructed by inserting an Spe1-BglII fragment from the h-βTrCP protein into vector pGAD1318, and the βTrCPΔF mutant (deleted residues: 32 to 179) was obtained by deleting the AvrII-Asp718 fragment of the h-βTrCP protein with conservation of the reading frame.

The following method was used to verify that the interaction between the Vpu and h-βTrCP proteins could take place in vitro: the two proteins were introduced into rabbit reticulocyte lyzate (RRL). The Vpu/TrCP complexes formed in vitro were identified by co-immunoprecipitation using anti-h-βTrCP antibodies directed against the peptide 553–569, which were prepared by the same method as that used to obtain the anti-h-βTrCP antibodies directed against the peptide 275–293.

Figure 3:
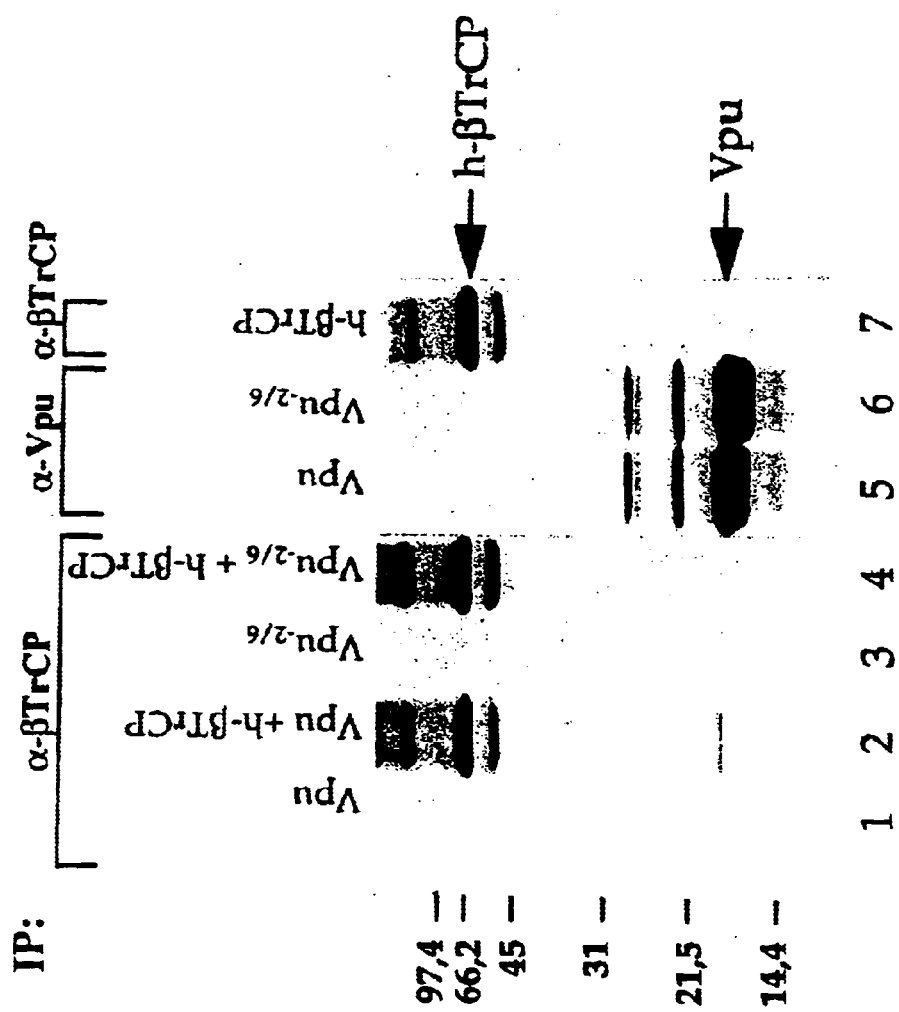
FIG. 3 is a photograph of a 15% SDS-PAGE gel showing the interaction between $Vp_c$ and the h-βTrCP protein of the invention, produced in vitro.

FIG. 3 illustrates the interaction between the Vpu and h-βTrCP proteins in vitro. Line 1 shows that the Vpu protein is not recognized by the anti-h-βTrCP antiserum, whereas line 5 shows that it precipitates in the presence of an anti-Vpu antiserum. Line 2 shows that the anti-h-βTrCP antibodies are capable of coprecipitating the Vpu protein cotranslated in vitro with the h-βTrCP protein. Line 4 shows that the double mutant of Vpu mutated in positions Ser52 and Ser56, which is incapable of inducing CD4 degradation, does not interact with the h-βTrCP protein and is not therefore coprecipitated by anti-h-βTrCP antibodies, whereas lines 6 and 7 show that this mutant, Vpu$_{c-2/6}$, is translated with the same efficacy as the Vpu protein.

TABLE

| Deletion mutants of h-βTrCP | Interaction with Vpuc |
|---|---|
| h-βTrCP: 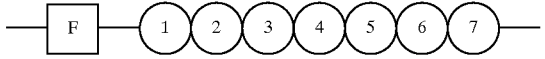 | +++ |
| VBP1: 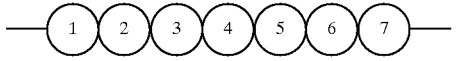 | +++ |
| VBP1-ΔW1: 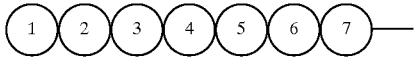 | − |
| VBP1-ΔC-ter:  | + |
| VBP1-ΔW4-7:  | + |
| h-βTrCP-Δ7W:  | − |

EXAMPLE 5

Interaction Between the h-βTrCP Protein and the Skp1p Protein

To demonstrate that the F-box unit was indeed functional and could therefore effectively be used for targeting towards proteasome via the Skp1p protein, a two-hybrid assay was performed between the N-terminal domain of the h-βTrCP protein and the Skp1p protein, making it possible to reveal an interaction between the h-βTrCP protein and the Skp1p protein.

The human Skp1p protein described by BAI et al. (1996, supra) was subcloned into vector pLex10 for analysis of the interaction with the h-βTrCP protein in the yeast strain L40 (VOJTEK et al., Cell, 74, 205–214, 1993).

FIG. 4 illustrates the results obtained. Line 1 of FIG. 4 shows first of all that the h-βTrCP protein interacts with the Skp1p protein. Line 2 shows that the N-terminal domain is sufficient to obtain the interaction, whereas line 3 shows that the absence of the N-terminal domain of the h-βTrCP protein in VBP1 removes all interaction with the Skp1p protein. These results are important additional arguments in favor of a role of the h-βTrCP protein in degradation of the CD4 receptor mediated by the Vpu protein, and also corroborate the results of FUJITA et al. (1997, supra) and SCHUBERT et al. (1997, supra), showing that degradation of the CD4 receptor induced by the Vpu protein ought to take place in proteasome. It should be nod that the CD4 cytoplasmic domain is incapable of binding directly to the Skp1 protein (line 4).

EXAMPLE 6

Model of the Network of Interactions Involved in Degradation of the CD4 Receptor Degradation of the CD4 receptor induced by the Vpu protein is effected by the network of interactions a) between the Vpu protein and the CD4 receptor, b) between the Vpu protein and the WD units of the h-βTrCP protein, and c) between the F-box of the h-βTrCP protein and the Skp1p protein, this last interaction allowing d) the targeting of the Vpu/CD4 complex towards proteasome.

Figure 5:
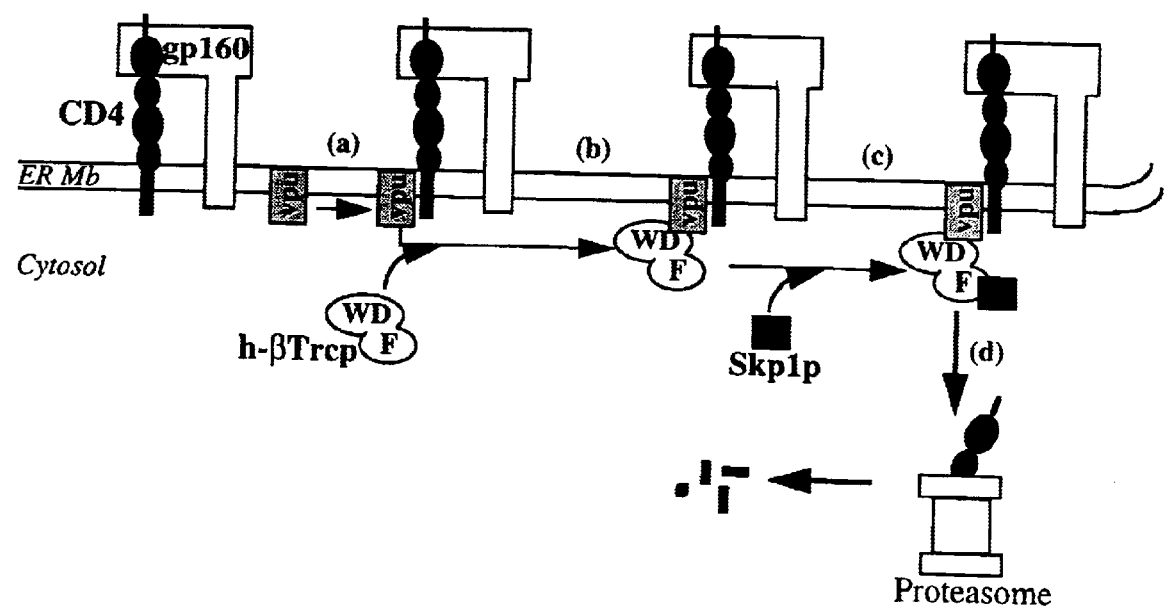
FIG. 5 is a schematic representation of the degradation of the CD4 receptor induced by the Vpu protein, showing the network of interactions described above.

This network of interactions is illustrated schematically in FIG. 5.

It is by way of such a network of interactions that degradation of the CD4 receptor by proteasome via the Vpu protein is caused.

Degradation of the CD4 receptor allows the release of the Gp160 envelope protein and hence the release of infectious FUV-1.

One of the means of preventing the development of HIV-1 in the affected patient therefore consists in preventing degradation of the CD4 receptor. One of the means of preventing this degradation in the light of the above degradation process consists in looking for inhibitors, or anti-HIV antiviral agents, which inhibit the interaction either between the Vpu protein and the h-βTrCP protein, or between the h-βTrCP protein and the Skp1p protein, by the processes described above.

EXAMPLE 7

Interaction Between the h-βTrCP Protein and the IκB Protein

For this yeast two-hybrid assay, the proteins described below were fused either to the Gal4 transcription activation domain (Gal4AD) or to the LexA DNA binding domain:

βTrCP=human βTrCP protein of the present invention,

IκBα,

IκBα S32-36A=IκBα mutant at serines S32 and S36 so that there is no phosphorylation, Ras=control protein, Raf=control protein, Vpuc=cytoplasmic Vpu protein as described above.

The experimental results which demonstrate the specific interaction of the novel human βTrCP protein with the IκB protein are illustrated in FIG. 6.

This two-hybrid assay shows that:

the two proteins h-βTrCP and IκB are capable of interacting, the h-βTrCP/IκB interaction is specific for the two hybrids since, when one of the two hybrids is replaced by a hybrid with another protein, such as Gal4AD-Raf or LexABD-Ras, there is no longer any interaction, whereas these two control hybrids are capable of interacting, and this interaction is removed when serine residues S32 and S36 of the IκB protein are mutated to non-phosphorylatable residues like alanine.

An interaction between the Vpu protein of HIV-1 and the h-βTrCP protein was also observed in this assay.

EXAMPLE 8

IκB/h-βTrCP interaction in human cells: modulation of the transcription activation of reporter genes for NFκB activity by Expression of the h-βTrCP Protein or its h-βTrCPΔF fragment In non-stimulated cells (NS) of the 293 cell line, the human βTrCP protein or the h-βTrCPΔF fragment is transitorily expressed from a eukaryotic expression vector such as pCDNA3 (Invitrogen), following insertion of the cDNA coding for the h-βTrCP protein under the control of a strong cytomegalovirus promoter (CMV). An amount of 3 μg of this plasmid permitting expression of the h-βTrCP protein or the h-βTrCPΔF fragment is cotransfected by lipofectamine (Life Technologies) with 1 μg of a reporter vector dependent on NFκB sites (3Enh-κB-ConA Luc) or independent of NFκB sites (RSV Luc or ConA Luc) which control the expression of the luciferase reporter gene.

Figure 7:
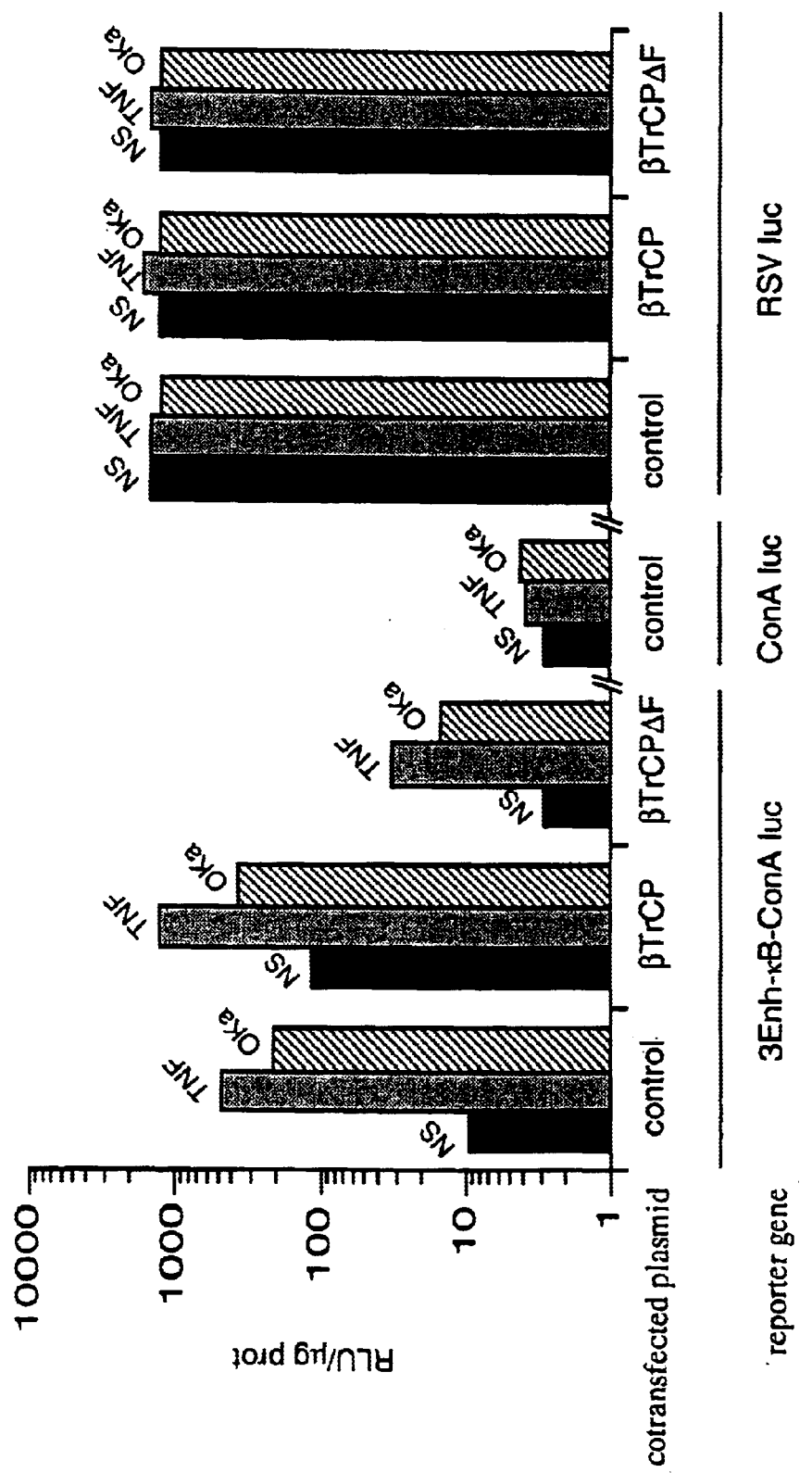
FIG. 7 is a graphic representation showing the expression of luciferase (in light units per μg: RLU/μg protein) in cells transfected with the constructs h-βTrCP and h-βTrCPΔF and the control plasmids and the following reporter vector: 3Enh-κB-ConA, ConA luc, RSV luc.

The results obtained (FIG. 7) show that the h-βTrCPΔF fragment is capable of acting as a negative transdominant. By competing with the endogenous βTrCP, the h-βTrCPΔF fragment inhibits the activation of NFκB induced by TNF or okadaic acid (OKA). This activation of NFκB is measured by the activity of a reporter gene under the control of a promoter which has three NFκB binding sites (3Enh-κB-ConA Luc) (Arenzana et al., 1993, J. Virol., 67, 6596–6609). On the other hand, the h-βTrCP protein has an activatory effect on the activation of NFκB. The h-βTrCP protein or the h-βTrCPΔF fragment has no effect on the transcription of a reporter gene directed by a promoter which does not contain NFκB sites (RSV Luc) (Invitrogen).

EXAMPLE 9

Use of Specific Antibodies for Revealing the Interaction Between the h-βTrCP Protein and the Endopenous IκB Protein of 293 or Hela Cells, and its consequences on the stability of the IκB protein The stability of the phosphorylated forms of IκB was analyzed in 293 cells 7i transfected by a control plasmid, by a pcDNA plasmid (Invitrogen) expressing the h-βTrCP protein, or by a pcDNA plasmid expressing the h-βTrCPΔF fragment, the h-βTrCP protein and the h-βTrCPΔF fragment having been fused to the myc epitope at the C-terminal end of this pcDNA vector. After 36 hours, the 293 cells were stimulated with TNF in the presence of 100 μg/ml of cycloheximide (protein synthesis inhibitor). The cytoplasmic proteins were separated on denaturing polyacrylamide gel/SDS and then transferred to a nitrocellulose membrane and incubated either with the 10B monoclonal antibody directed against the amino terminal part of IκB and recognizing all forms of the protein (α-IκBα; JAFFRAY et al., Mol. Cell. Biol., 15, 2166–2172, 1995), or with a polyclonal antibody specifically recognizing the phosphorylated forms of IκB (α-IκBα-S32®; 9241S, New England Biolabs), or with an anti-myc monoclonal antibody directed against the myc epitope fused to h-βTrCP and h-βTrCPΔF and showing the expression of the latters in the transfected cells (α-Myc; SC40AC, Santa Cruz), by carrying out a Western blot (WB).

Figure 8:
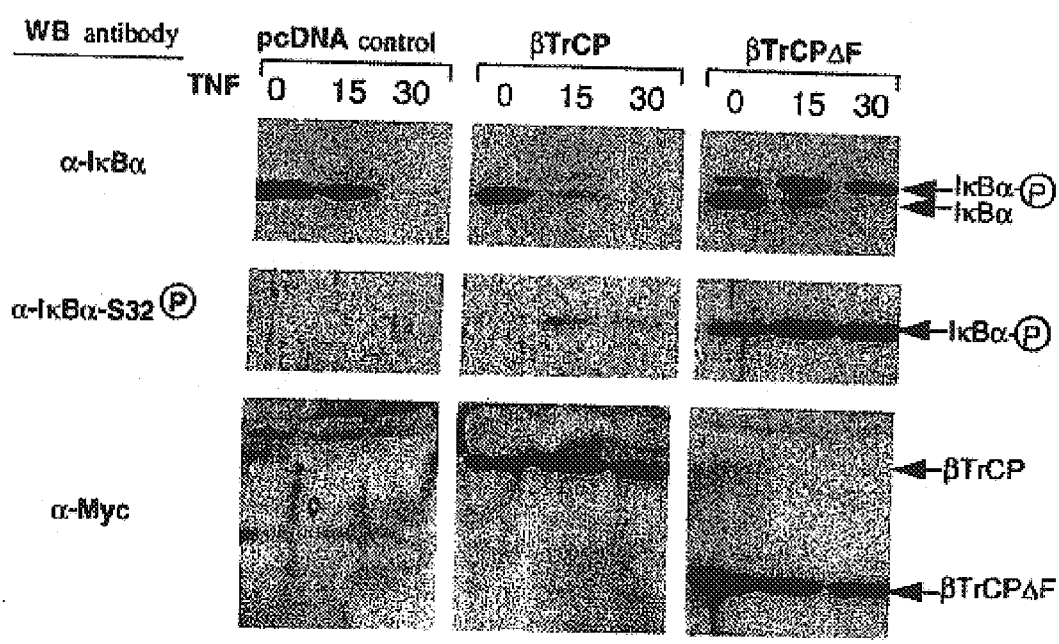
FIG. 8 is a photograph of an immunoblot showing the detection of the phosphorylated or non-phosphorylated IκB protein and the h-βTrCP protein or the h-βTrCPΔF fragment, in the presence of anti-IκBα, anti-IκBα-S32® and anti-Myc antibodies.

The results obtained (FIG. 8) show that the expression of the h-βTrCPΔF mutant is accompanied by inhibition of the degradation of IκB normally induced by TNF. Under the influence of the expression of h-βTrCPΔF, the phosphorylated forms accumulate, as shown by the reactivity of the α-IκBα-S32® antibodies (right panel).

The h-βTrCP protein, on the other hand, activates the degradation of IκBα (middle panel). The bottom panel, relating to the α-Myc antibody, is a control panel showing the expression of the h-βTrCP and h-βTrCPαF proteins.

The h-βTrCP/IκB interaction was also confirmed by an immunoprecipitation experiment.

To do this, Hela cells were transfected with a control pcDNA plasmid expressing β-galactosidase (β-Gal), the h-βTrCP protein (βTrCP) or the h-βTrCPΔF mutant (βTrCPΔF), h-βTrCP and h-βTrCPΔF having been fused to an myc epitope at the C-terminal end. After 36 hours, the Hela cells were stimulated for 15 minutes with TNF in the presence of proteasome inhibitors (z-LLL-H) (PALOMBELLA V. et al., Cell, 78, 773–789, 1994) (z-LLL-H+TNF; +reaction) or left without stimulation (−reaction). The subsequent procedure then consisted either of a direct immunoblot after separation of the proteins in the cell lyzate on denaturing gel/SDS and transfer to a nitrocellulose membrane incubated with α-IκBa-S32® antibodies (top panel), or to an immunoprecipitation with α-Myc antibodies followed by an immunoblot, as indicated above, with the α-IκBα-S32® antibody or the α-IκBα antibody.

Figure 9:
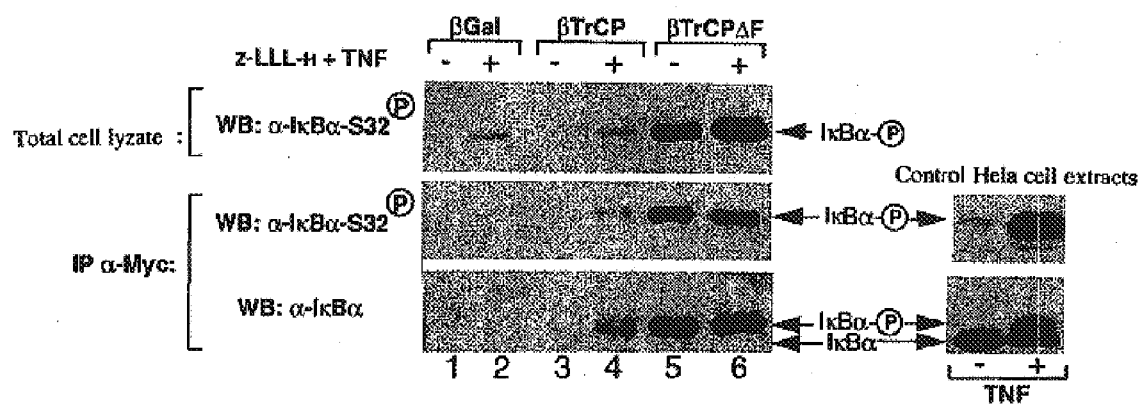
FIG. 9 is a photograph of an immunoblot showing the detection of the phosphorylated or non-phosphorylated IκB protein with the h-βTrCP protein or the h-βTrCPΔF fragment, in the presence of anti-IκBa-S32® and anti-IκBα antibodies.

The results are indicated in FIG. 9, in which the top panel shows the results of the Western blot only and the bottom two panels show those of the immunoprecipitation/Western blot, and the right panel gives the pattern of migration of the phosphorylated forms induced by treatment with TNF on control Hela cells.

By means of experiments involving the co-immunoprecipitation of the h-βTrCP protein or the h-βTrCPΔF fragment fused to the myc epitope, FIG. 9 shows that only the phosphorylated form of IκBα, and not the non-phosphorylated form, is associated with the h-βTrCP protein (column 4). This association is disclosed especially through the inhibition of degradation induced by the h-βTrCPΔF mutant (columns 5 and 6) and the use of proteasome inhibitors (z-LLL-H).

EXAMPLE 10

Interaction Between the h-βTrCP Protein and the β-catenin Protein

For this two-hybrid assay, the cDNAs coding for the proteins described below were fused either to the Gal4 transcription activation domain (Gal4AD) or to the LexA DNA binding domain (LexABD):

βTrCP=human βTrCP protein of the present invention,

KIAA 0696 (βTCP2)=human βTrCP protein isolated by ISHIKAWA et al. (DNA Research, 5, 169–176, 1998), βCat$_{1 \to 130}$=normal β-catenin protein (N-terminal domain; 1→130), βCat$_{1 \to 130}$ S33-37AA=oncogenic β-catenin protein mutated on serine residues S33 and S37 so that there is no phosphorylation, βCat=whole normal β-catenin protein.

Figure 10:
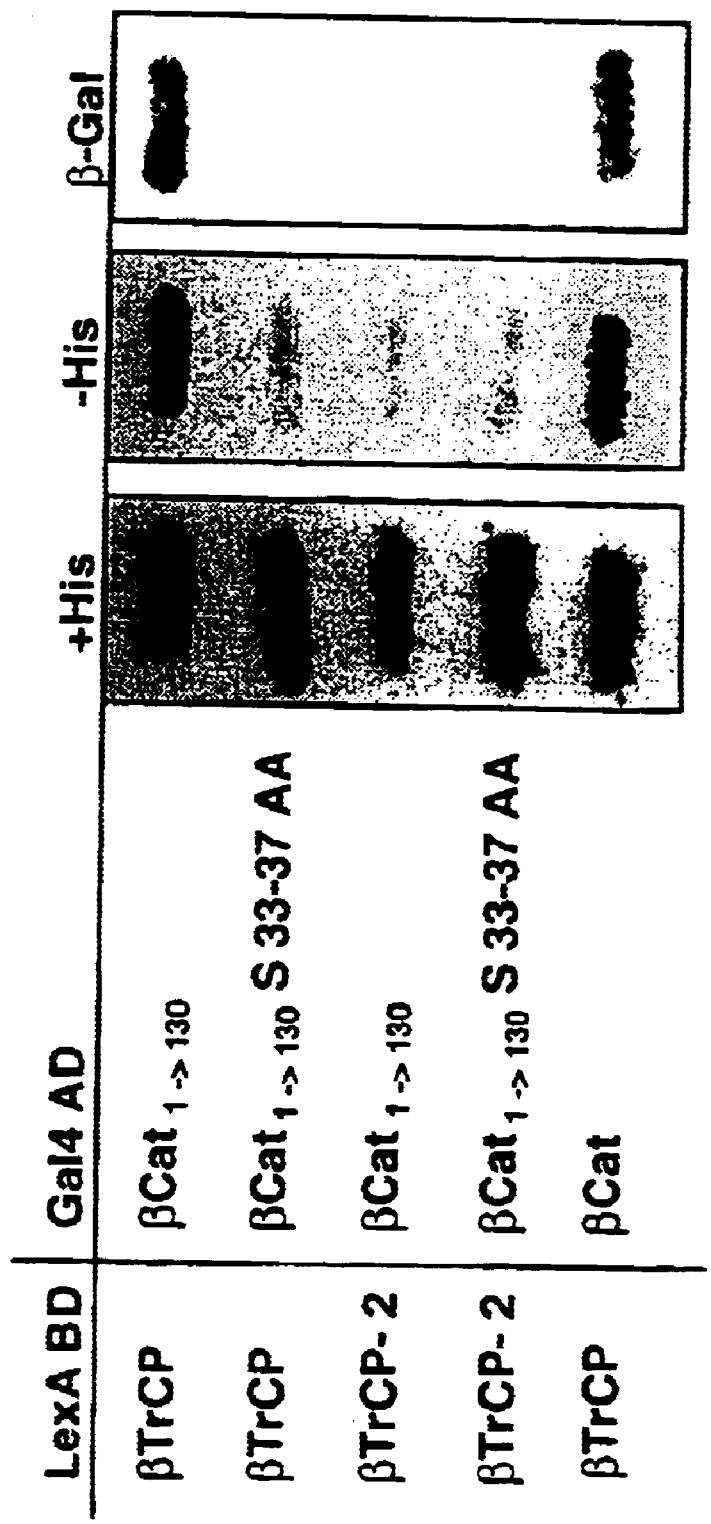
FIG. 10 is a photograph of a Petri dish showing the growth of yeast cells cotransformed by plasmids containing βTrCP+ βCat$_{1\to130}$, βTrCP+βCat$_{1\to130}$ S33-37AA, βTrCP2+ βCat$_{1\to130}$, βTrCP2+βCat$_{1\to130}$ S33-37AA and βTrCP+ βCat, on His+ medium, on His− medium and the expression of β-Gal.

The experimental results, which demonstrate that there is a specific interaction of the novel human βTrCP protein with the β-catenin protein, are illustrated in FIG. 10.

This two-hybrid assay shows that:

the two proteins h-βTrCP and βCat$_{1\to130}$ are capable of interacting, the h-βTrCP/βCat$_{1\to130}$ interaction is removed when serine residues S33 and S37 are mutated to non-phosphorylatable residues (oncogenic β-catenin), and βTrCP2 is not capable of reacting either with non-mutated β-catenin or with mutated β-catenin.

It should be noted that an interaction is also observed between the whole β-catenin protein and the h-βTrCP protein.

EXAMPLE 11

Activation of the Transcription of the TCF/LEF Reporter Gene by the Expression of Mutated β-catenin or h-βTrCPΔF in Human 293 Cells HEK 293 cells were transfected with reporter vector TopTK-Luci, which contains a multimer of TCF-LEF sites, or reporter vector Fop-TK-Luci, which contains an inactive control multimer of TCF-LEF sites. These constructs are cotransfected with expression vector pCDNA3 (Invitrogen), either void as control, or expressing a oncogenic β-catenin fragment, namely β-catenin devoid of the N-terminal part, βCatAN, or expressing the h-βTrCP protein or the βTrCpΔF fragment. The luciferase activity is measured 24 h after transfection and standardized to a control Renilla luciferase activity obtained by the cotransfection of cells with vector RSV-Renilla (Promega).

Figure 11:
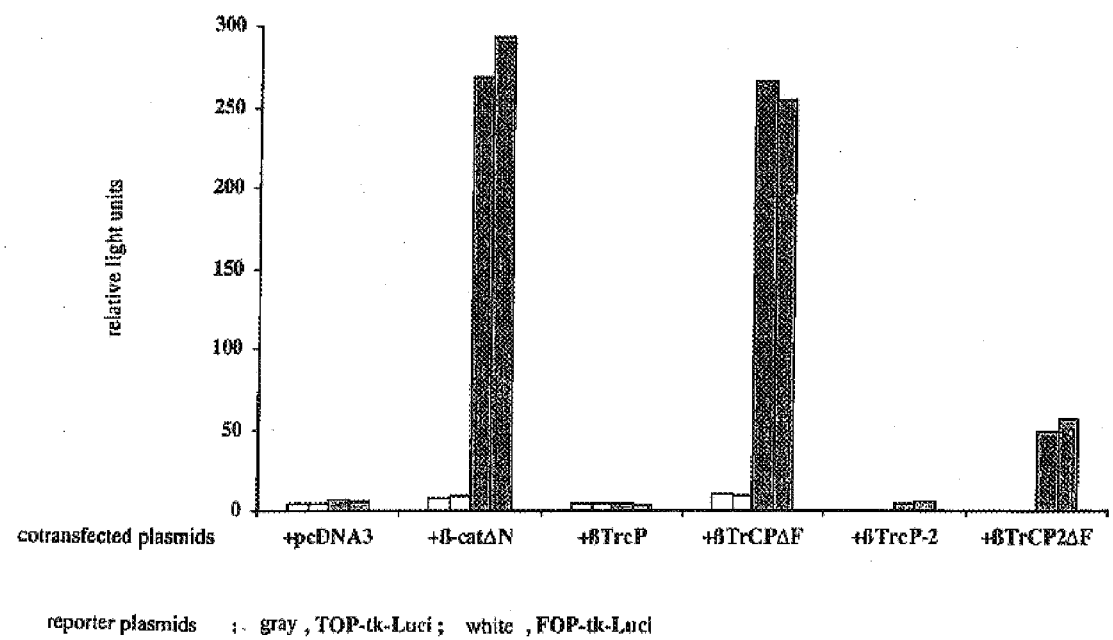
FIG. 11 is a graphic representation showing the expression of luciferase (RLU/μg protein) in cells transfected with plasmid pcDNA3 and plasmids containing βCatΔN, βTrCP, BTRCPΔF, KIA 696 (βTrCP2) and KIA 696 ΔF (βTrCP2ΔF)

The results obtained, which are given in FIG. 11, show that the h-βTrCPΔF fragment induces the activation of a reporter gene controlled by a TCF/LEF promoter, which responds to modifications in β-catenin expression level (Morin P. J. et al., 1997, Science, 275, 1787–1790). This indicates that the degradation of β-catenin is inhibited by expression of the h-βTrCPΔF mutant. On the other hand, as regards the KIAA 0696 protein, βTrCP2, in the same reporter gene system, the positive effect induced by KIAA 0696 ΔF (βTrCP2ΔF) is much weaker than that obtained with the equivalent βTrCpΔF construct.

Taken together, these results therefore demonstrate that it is the h-βTrCP protein of the invention, and not the KIAA 0696 protein, which is the mediator of β-catenin degradation.

EXAMPLE 12

Figure 12:
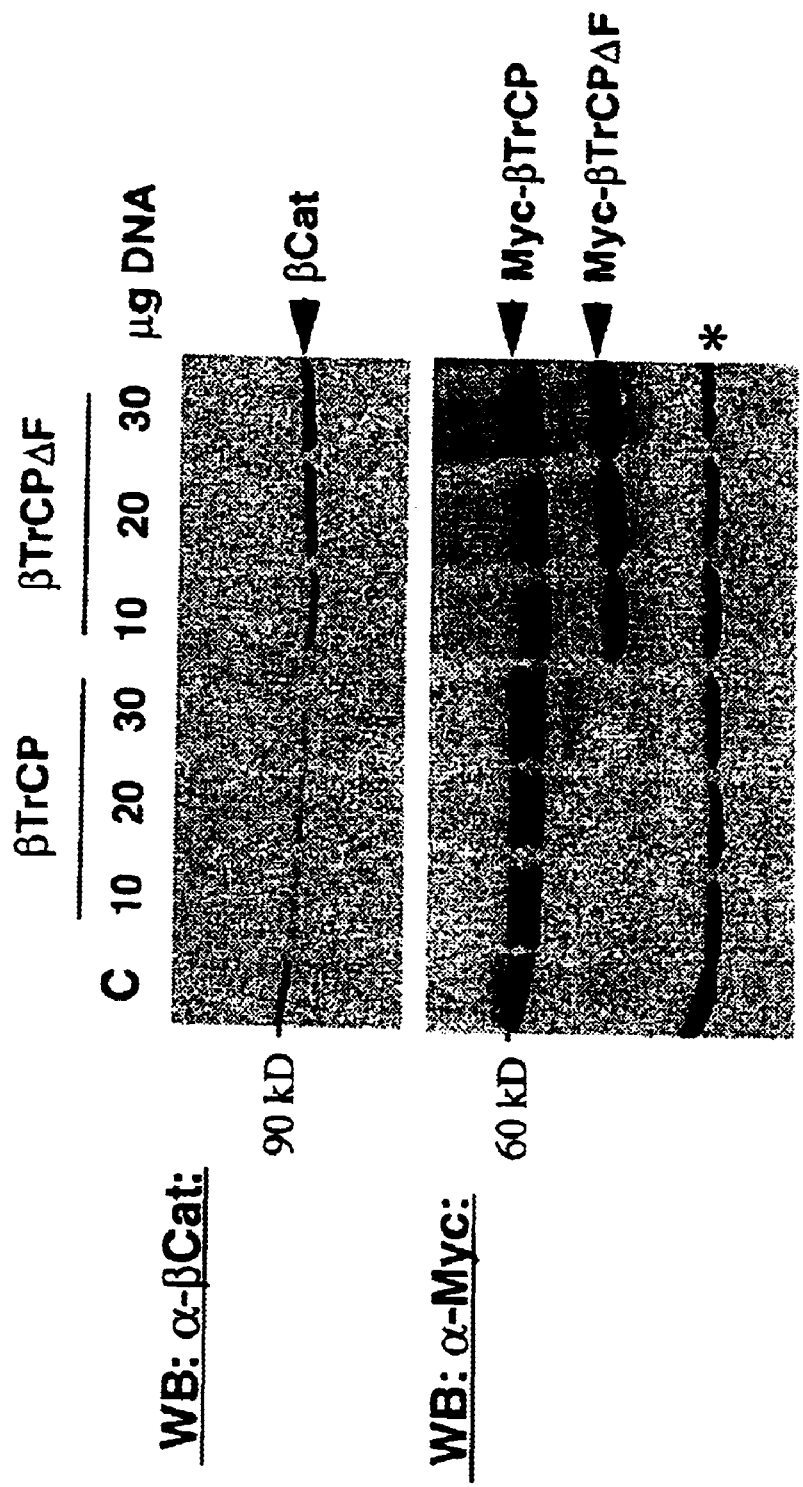
FIG. 12 is a photograph of an immunoblot showing a study of the stability of the β-catenin protein detected with anti-βCat antibodies under the influence of the expression of the h-βTrCP protein or the h-βTrCPΔF fragment detected by the anti-Myc antibody.

Study of the Expression of the h-βTrCP Protein or the h-βTrCPΔF Fragment on the Stability of the Endogenous β-catenin of Hela Cells Hela cells were transfected with the amounts of DNA indicated in FIG. 12, expressing either the h-βTrCP protein or the h-βTrCPΔF fragment fused to the myc epitope at the C-terminal end in a pcDNA vector (Invitrogen). After 24 hours, the cells were lyzed and the cell proteins were separated on denaturing polyacrylamide gel/SDS, transferred to a nitrocellulose membrane and incubated either with an anti-β-catenin antibody (α-βCat), or with an anti-myc antibody for detecting the expression of the h-βTrCP protein or the h-βTrCPΔF fragment (α-Myc), by carrying out a Western blot (WB).

The results are indicated in FIG. 12 and show that the expression of h-βTrCP increases the degradation of β-catenin (middle column), whereas the expression of the h-βTrCPΔF mutant inhibits the degradation of β-catenin and leads to its accumulation in the cells (right column).

It should be noted that column C shows a control of non-transfected Hela cells; the asterisk indicates, by the non-specific labeling of a cell protein in the Hela cell lyzate, that approximately the same amount of cell proteins has been deposited in all the lanes.

The results corroborate those shown in the previous Example.

What is claimed is:

1. Human βTrCP protein (h-βTrCP) for the targeting of proteins towards proteasome degradation pathways, said protein having SEQ ID NO:2 and being capable of interacting with proteins degradable by proteasome, which possess the phosphorylation unit comprising the amino acids Asp-Ser-Glu-Xaa-Xaa-Ser (SEQ ID NO:9), in which Xaa is any natural amino acid and the serine residues are phosphorylated and said protein comprising the following units having the following positions in the sequence SEQ ID NO:2:

| | |
|---|---|
| F-box: | amino acids 147–191, |
| first WD unit: | amino acids 259–292, |
| second WD unit: | amino acids 304–332, |
| third WD unit: | amino acids 343–373, |
| fourth WD unit: | amino acids 387–415, |
| fifth WD unit: | amino acids 427–455, |
| sixth WD unit: | amino acids 467–492, and |
| seventh WD unit: | amino acids 516–544. |

2. Protein according to claim 1, characterized in that it is capable of interacting with the Vpu protein of HIV-1 virus or with the cell proteins Iκβ or β-Catenin.

3. Protein according to claim 1, characterized in that it is capable of interacting with the Skp1p protein.

4. A nucleic acid sequence coding for the human protein h-βTrCP according to claim 1, characterized in that it consists of:

a) the DNA sequence of SEQ ID NO:1;

b) a DNA sequence which codes for the human protein h-βTrCP having SEQ ID NO:2; or c) a mRNA or cDNA sequence corresponding to a) or b).

5. Expression vector, characterized in that it comprises a nucleic acid sequence according to claim 4 and the means necessary for its expression.

6. Microorganisms or host cells transformed by an expression vector according to claim 5.

7. A method of identifying anti-HIV-1 antiviral agents, the method comprising the step of screening anti-HIV antiviral agent candidates using the h-βTrCP protein of claim 1 to determine the capability of the anti-HIV antiviral agent candidates to inhibit the interaction between h-βTrCP protein and Vpu protein, wherein an anti-HIV antiviral agent candidate that inhibits binding between h-βTrCP protein and Vpu protein is identified as an anti-HIV-1 antiviral agent.

* * * * *